US008255225B2

(12) United States Patent
Byford et al.

(10) Patent No.: US 8,255,225 B2
(45) Date of Patent: Aug. 28, 2012

(54) VOICE ASSISTANT SYSTEM

(75) Inventors: Roger Graham Byford, Apollo, PA (US); David M. Findlay, Freeport, PA (US); Michael Laughery, Monroeville, PA (US); James R. Logan, Pittsburgh, PA (US); Mark B. Mellott, Pittsburgh, PA (US); James E. Shearon, Pittsburgh, PA (US); Kathleen A. Tellish, Hookstown, PA (US); Christopher M. Winters, Pittsburgh, PA (US)

(73) Assignee: Vocollect Healthcare Systems, Inc., Pittsburgh, PA (US)

(*) Notice: Subject to any disclaimer, the term of this patent is extended or adjusted under 35 U.S.C. 154(b) by 382 days.

(21) Appl. No.: 12/536,696

(22) Filed: Aug. 6, 2009

(65) Prior Publication Data

US 2010/0036667 A1     Feb. 11, 2010

Related U.S. Application Data

(60) Provisional application No. 61/087,082, filed on Aug. 7, 2008.

(51) Int. Cl.
*G10L 21/00* (2006.01)
(52) U.S. Cl. ......... 704/275; 704/231; 704/258; 704/270
(58) Field of Classification Search .................. 704/231, 704/258, 370, 270, 275
See application file for complete search history.

(56) References Cited

U.S. PATENT DOCUMENTS

| | | | |
|---|---|---|---|
| 4,213,253 A | | 7/1980 | Gudelis |
| 4,629,015 A | * | 12/1986 | Fried et al. ................. 177/25.19 |
| 5,077,666 A | | 12/1991 | Brimm et al. |
| 5,536,084 A | | 7/1996 | Curtis et al. |
| 5,754,111 A | | 5/1998 | Garcia |
| 5,822,544 A | * | 10/1998 | Chaco et al. ..................... 705/2 |

(Continued)

FOREIGN PATENT DOCUMENTS

EP     1791053     5/2007

(Continued)

OTHER PUBLICATIONS

Forty-Seven-page "The Digital Consumer Technology Handbook", A Comprehensive Guide to Devices, Standards, Future Directions, and Programmable Logic Solutions; by Amit Dhir, Xilinx, Inc., 2004.

(Continued)

*Primary Examiner* — Douglas Godbold
(74) *Attorney, Agent, or Firm* — Wood, Herron & Evans, LLP

(57) ABSTRACT

Methods and apparatuses to assist a user in the performance of a plurality of tasks are provided. The method may comprise storing at least one care plan in a voice assistant, the care plan defining a plurality of tasks to be performed, capturing speech input from the user, determining, from the speech input, a selected interaction with a care plan, and in response to the selected interaction, providing a speech dialog with the user reflective of the care plan. Alternatively, the method may comprise capturing speech input from a user, determining from the speech input, a first weight associated with a resident, associating the first weight with a care plan in turn associated with the resident, comparing the first weight to a second weight associated with the resident and the care plan, and providing a speech dialog regarding reweighting the resident based on the comparison.

70 Claims, 33 Drawing Sheets

U.S. PATENT DOCUMENTS

| | | | |
|---|---|---|---|
| 5,838,223 A * | 11/1998 | Gallant et al. | 340/286.07 |
| 5,853,377 A * | 12/1998 | Madsen et al. | 600/587 |
| 5,986,568 A * | 11/1999 | Suzuki et al. | 340/9.1 |
| D420,674 S | 2/2000 | Powell | |
| 6,057,758 A | 5/2000 | Dempsey et al. | |
| 6,292,783 B1 | 9/2001 | Rohler et al. | |
| 6,591,242 B1 | 7/2003 | Karp et al. | |
| 6,714,913 B2 * | 3/2004 | Brandt et al. | 705/2 |
| 6,720,864 B1 | 4/2004 | Wong et al. | |
| 6,747,556 B2 * | 6/2004 | Medema et al. | 340/539.12 |
| 6,772,454 B1 | 8/2004 | Barry | |
| 6,849,045 B2 * | 2/2005 | Iliff | 600/300 |
| 6,872,080 B2 * | 3/2005 | Pastrick et al. | 434/262 |
| 6,890,273 B1 | 5/2005 | Perez | |
| 7,065,381 B2 | 6/2006 | Jenkins | |
| 7,228,429 B2 | 6/2007 | Monroe | |
| 7,283,845 B2 | 10/2007 | De Bast | |
| 7,287,031 B1 | 10/2007 | Karpf | |
| D568,881 S | 5/2008 | Hsiau | |
| D569,358 S | 5/2008 | Devenish, III et al. | |
| D569,876 S | 5/2008 | Griffin | |
| D573,577 S | 7/2008 | Huang | |
| D583,827 S | 12/2008 | Wahl | |
| 7,574,370 B2 | 8/2009 | Mayaud | |
| D609,246 S | 2/2010 | Wahl | |
| 7,664,657 B1 * | 2/2010 | Letzt et al. | 705/2 |
| 2002/0004729 A1 | 1/2002 | Zak et al. | |
| 2002/0146096 A1 | 10/2002 | Agarwal et al. | |
| 2003/0182117 A1 * | 9/2003 | Monchi et al. | 704/237 |
| 2003/0208357 A1 * | 11/2003 | Hammond | 704/270 |
| 2004/0220686 A1 | 11/2004 | Cass | |
| 2006/0200354 A1 * | 9/2006 | Ito et al. | 704/275 |
| 2006/0253281 A1 * | 11/2006 | Letzt et al. | 704/231 |
| 2007/0073168 A1 * | 3/2007 | Zhang et al. | 600/483 |
| 2007/0219806 A1 * | 9/2007 | Yamaki | 704/275 |
| 2007/0221138 A1 | 9/2007 | Mainini et al. | |
| 2008/0072847 A1 | 3/2008 | Liao | |
| 2008/0082338 A1 * | 4/2008 | O'Neil et al. | 704/275 |
| 2009/0171667 A1 * | 7/2009 | Rivera | 704/275 |
| 2009/0177477 A1 * | 7/2009 | Nenov et al. | 704/275 |
| 2009/0216534 A1 | 8/2009 | Somasundaram | |
| 2010/0026817 A1 * | 2/2010 | Ryan et al. | 348/207.11 |
| 2010/0052871 A1 | 3/2010 | Somasundaram et al. | |
| 2010/0286490 A1 * | 11/2010 | Koverzin | 600/301 |

FOREIGN PATENT DOCUMENTS

| | | |
|---|---|---|
| WO | WO9525326 | 9/1995 |
| WO | WO02096126 | 11/2002 |
| WO | WO2005043303 | 5/2005 |

OTHER PUBLICATIONS

Forty-Seven-page "The Digital Consumer Technology Handbook", A Comprehensive Guide to Devices, Standards, Future Directions, and Programmable Logic Solutions; by Amit Dhir, Xilinx, Inc. dated Feb. 27, 2004.

* cited by examiner

You are here . . . > Residents > Jane Doe > Toileting

Toileting

I want to... ▶

Physical Functioning - Bowel
*SELECTED: Continence bowel: Usually continent; Level of support bowel: One person physical assist; Self-performance bowel: Limited assistance.*

Self-performance: [Limited assistance ▶]
Level of support provided: [One person physical assist ▶]
Continence: [Usually continent ▶]

Physical Functioning - Bladder
*SELECTED: Continence bladder: Occasionally incontinent; Level of support bladder: One person physical assist; Self-performance bladder: Limited assistance.*

Self-performance: [Limited assistance ▶]
Level of support provided: [One person physical assist ▶]
Continence: [Occasionally incontinent ▶]

Cautions
*SELECTED: Do not leave unattended in bathroom; High risk for falls.*

☒ Do not leave unattended in bathroom
☒ High risk for falls
☐ Assistance needed for toileting transfer
☐ Notify nurse if dressing soiled or removed

Monitoring
*SELECTED: Scheduled toileting.*

Set up a schedule:
○ None
◉ Scheduled toileting
   ✗ 12:00 PM
   ✗ 2:00 PM
   [Select time... ▶] [AM/PM... ▶] Add another?
○ Bladder training program

Check and change briefs

Starts: [____] 📅
Repeats: [Select time... ▶] [Select time... ▶] [AM/PM... ▶]
Ends: ◉ Never
       ○ Until

---

Brown, John
CNA, Meadowlark Lemon Estates
logout

[People Search]

Jane Anne Doe
postion: chair
May 13, 3:53 PM

- Site
- Unit
- Residents
- Staff
- Reports
- About

☐ Record urine output in ccs
Special Equipment
*No summary found.*
☐ Uses bedside commode or urinal
Uses bedpan: [Does not use bedpan ▶]
Uses catheter: [Does not use catheter ▶]
Briefs
*SELECTED: uses standard briefs.*
○ None
⦿ Uses standard briefs   [Medium ▶]
○ Uses special briefs
☐ Family suppplies incontinense product
Incontinence
*SELECTED: Apply barrier cream to perineal area; Pericare after incontinent episode.*
☑ Uses bedside commode or urinal
[Apply barrier cream to perineal area. ▶]
Ostomy Care
*No summary found.*
☑ Has colostomy bag
☑ Independent with colostome care
☐ Has urostomy bag
☐ Independent with ostomy care
☐ Notify nurse when care required
Custom Notes
*No custom notes.*
Custom Notes
None available.
Add New Note

*Notes longer than 1000 characters will be truncated.*
Expires:
⦿ Never
○ Date: [    ] 🔢

[Save my changes] [Do not save my changes]

FIG. 2B

"SELECT ROOM..."
"REVIEW"

"DOCUMENT"

| | |
|---|---|
| AMBULATION | BACKGROUND |
| BATHING | CARE |
| DRESSING | PAGES |
| HYGIENE | REMINDERS |
| MEALS | UPDATES |
| MOOD | END OF SHIFT |
| BEHAVIOR | REPORTS |
| POSITIONING | MEDICAL |
| RESTORATIVE | PRECAUTIONS |
| TOILETING | |
| TRANSFERS | |
| VITALS | |

"RECORD"

CLINICAL NOTE
END OF SHIFT REPORTS (Nurses Only)
WELCOME MESSAGE (Nurses Only)

| Self-performance? | Support? |
|---|---|
| Independent | None, Setup |
| Supervison | None, Setup |
| Limited | One-person |
| Extensive | One or Two-person |
| Total | One or Two-person |

HELP
SLEEP
NOISE SAMPLE

"WHO?"

...ARE MY RESIDENTS?
...HAS UPDATES?
...HAS APPOINTMENTS?
...NEEDS VITALS?
...NEEDS BATHING?
...NEEDS CARE?
...NEEDS RESTORATIVE?

"PAGE"

"STAFF MEMBER NAME"
UNIT (for all staff on unit)
SITE (for all staff in facility)
FOR ROOM...

"REVIEW LAST"

| | |
|---|---|
| WEIGHT | MEALS |
| URINE | VITALS |
| BM | FLUIDS |

Background

Cautions
*No summary found.*
☐ Resident smokes. Do not let resident smoke unattended.

Special Equipment
*No summary found.*
☐ Oxygen equipment needed

Personal Information
*No summary found.*
Lived Alone Prior to Entry
Lifetime Occupation(s)
Marital Status
Highest Education Level Completed

[Select prior living status...]
[Select current marital status...]
[Select education level...]

Mental Status
*No summary found.*
☐ Is resident comatose?

Memory
☐ Short-term memory impaired
☐ Long-term memory impaired

Decision Making
[Select decision making skills...]

Vision and Hearing
*No summary found.*

Approaches to Mental Status
☐ Requires extra time and patience
☐ Approach calmly
☐ Requires reorientation
☐ Responds to validation I want to... ▶

FIG. 13A

Vision

Select vision ability... ▼

<u>Left Eye</u>
☐ Blind
☐ Artificial
☐ Requires use of glasses, contact lenses, etc.

<u>Right Eye</u>
☐ Blind
☐ Artificial

Routines
*No summary found!*

Sleep Patterns
☐ Stays up late at night (e.g., after 9pm)
☐ Naps regularly during day for at least 1 hour
☐ Sleeps all night
☐ Exhibits wandering behavior
☐ Elevate head of bed

Rest Patterns
☐ Morning
☐ Afternoon
☐ Evening

Speech
*No summary found!*

Primary Language
Select primary language... ▼

Speech
Select speech quality... ▼

Hearing

Select hearing ability... ▼

<u>Left Ear</u>
☐ Hearing Aid
☐ Deaf

<u>Right Ear</u>
☐ Hearing Aid
☐ Deaf

Customary Routine
Stays busy with the following activities:

☐ Hobbies
☐ Reading
☐ Music
☐ Games
☐ Family members visit regularly

☐ Welcomes pet visits
☐ Fixed routine
☐ TV
☐ Welcomes day care children

Secondary Language
Select secondary language... ▼

Ability to understand others
Select ability to understand... ▼

FIG. 13B

Bathing

I want to... ▶

Physical Functioning
*No summary found.*

Self-performance: [Select self-performance...]
Level of support provided: [Select level of support...]

Cautions
*No summary found.*

☐ Assistance needed for transfer
☐ Uses special shampoo
☐ Uses special soap
☐ Wrap cast in plastic before bathing
☐ Water temperature no higher than 100 F
☐ Do not wash hair

Monitoring
*No summary found.*

☐ Before bathing, check entire body and report warm, discolored or open skin areas
☐ Test and reapply bed or chair alarm

Scheduled care:

| | Sunday | Monday | Tuesday | Wednesday | Thursday | Friday | Saturday |
|---|---|---|---|---|---|---|---|
| Nail care | -Shift- | -Shift- | -Shift- | -Shift- | -Shift- | -Shift- | -Shift- |
| Shower | -Shift- | -Shift- | -Shift- | -Shift- | -Shift- | -Shift- | -Shift- |
| Bed bath | -Shift- | -Shift- | -Shift- | -Shift- | -Shift- | -Shift- | -Shift- |
| Tub bath | -Shift- | -Shift- | -Shift- | -Shift- | -Shift- | -Shift- | -Shift- |

FIG. 14

Dressing

I want to...

Physical Functioning
*No summary found.*

Self-performance: [Select self-performance...]
Level of support provided: [Select level of support...]
☐ Selects own clothes
☐ Able to make needs known
Assist with extremities: ☐ Upper ☐ Lower

Cautions
*No summary found.*

Dress dependent side first: [Select side...]
☐ Follow hip precautions

Monitoring
*No summary found.*

☐ Before dressing, check entire body and report warm, discolored or open skin areas
☐ After undressing, check entire body and report warm, discolored or open skin areas
☐ Test and reapply bed or chair alarm Dress resident      ☐ Day ☐ Evening ☐ Night
Undress resident    ☐ Day ☐ Evening ☐ Night
Lay out clothing    ☐ Day ☐ Evening ☐ Night

Special Equipment
*No summary found.*

☐ Has artificial limb?

Uses dressing aids:
☐ Reacher
☐ Sock aid
☐ Dressing stick
☐ Long-handled shoe horn

Wears:
☐ Hip pads
☐ Adaptive clothing
☐ Adaptive shoes
☐ Knee-high stockings
☐ Thigh-high stockings
☐ Non-skid socks
☐ Sports bra

FIG. 15

Personal Hygiene

I want to... ▶

Physical Functioning
*No summary found.*

Self-performance: [Select self-performance...]
Level of support provided: [Select level of support...]

Cautions
☐ Rinse dentures thoroughly after soaking
☐ Report any mouth wash that contains alcohol
☐ Monitor and report mouth ulcers
☐ Check with nurse before grooming

Monitoring
*No summary found.*

Denture care
On [Select shift...] shift, [  ] times

Tooth care
On [Select shift...] shift, [  ] times

Total mouth care
On [Select shift...] shift, [  ] times

Apply vaseline to lips
On [Select shift...] shift, [  ] times

FIG. 16A

Special Equipment
*No summary found.*
Upper dentures: [Select...▼]
Lower dentures: [Select...▼]
☐ Assist with inserting dentures
☐ Use denture adhesive
☐ Soak dentures in cleanser at bedtime
☐ Use easy gel mouth care product
☐ Use toothettes as needed
☐ Use glycerin swabs as needed
Shaving: [Select razor type...▼]

AM/PM/Extra Care
*No summary found.*

| | AM CARE [Select shift...▼] | PM CARE [Select shift...▼] | EXTRA CARE | | |
|---|---|---|---|---|---|
| | | | Day | Evening | Night |
| Apply hand lotion | ☐ | ☐ | ☐ | ☐ | ☐ |
| Brush hair | ☐ | ☐ | ☐ | ☐ | ☐ |
| Check and clean glasses | ☐ | ☐ | ☐ | ☐ | ☐ |
| Check hearing aid | ☐ | ☐ | ☐ | ☐ | ☐ |
| Glasses at bedside | ☐ | ☐ | ☐ | ☐ | ☐ |
| Hearing aid kept in room | ☐ | ☐ | ☐ | ☐ | ☐ |
| Hearing aid kept on med cart | ☐ | ☐ | ☐ | ☐ | ☐ |
| Remove dentures | ☐ | ☐ | ☐ | ☐ | ☐ |
| Remove hearing aid | ☐ | ☐ | ☐ | ☐ | ☐ |
| Remove TED stockings and provide foot care | ☐ | ☐ | ☐ | ☐ | ☐ |
| Replace dentures | ☐ | ☐ | ☐ | ☐ | ☐ |
| Replace hearing aid | ☐ | ☐ | ☐ | ☐ | ☐ |
| Shave with razor | ☐ | ☐ | ☐ | ☐ | ☐ |
| Use body cream or lotion | ☐ | ☐ | ☐ | ☐ | ☐ |
| Wig care | ☐ | ☐ | ☐ | ☐ | ☐ |

FIG. 16B

Meals

Physical Functioning
*No summary found.*

Self-performance: [Select self-performance...▼]
Level of support provided: [Select level of support...▼]

Cautions
*No summary found.*

☐ NPO at all times
☐ No straw
☐ Chewing difficulty
☐ Swallowing problem
Thickened liquids: [Does not use thickened liquids ▼]
☐ Aspiration precautions
☐ Keep head of bed raised 30 degrees or higher after meals

Daily fluid restriction
Day [ ]
Evening [ ]
Night [ ]

Monitoring
*SELECTED: Record meal intake in percent.*
☑ Record meal intake in percent
☐ Record fluid intake in CCs

Clear liquids
for [ ] hours, starting at [Select time...▼] [AM/PM...▼] on [ ]

NPO
for [ ] hours, starting at [Select time...▼] [AM/PM...▼] on [ ]

Feeding tube: [Does not use feeding tube ▼]
☐ Uses IV
☐ No water pitcher at bedside
☐ Eats better alone in dining room
Clean pockets between gums and cheeks:
☐ After meals
☐ After snacks I want to... ▼

FIG. 17A

Offer beverage

Starts: [ ] [Select time...] [AM/PM.]

Repeats: [Does not repeat]

Ends: ⦿ Never  ◯ Until

Snacks:
[ ] Requires snacks/supplements for medical reasons
Type: [Select a snack type...]

Special Equipment
*No summary found*
[ ] Uses special utensils
[ ] Uses divided plate
[ ] Provide wash cloth before and after eating

Diet Options
*No summary found*

Diet Type:
⦿ None
◯ House
◯ Mechanical soft
◯ Pureed

[ ] Clear liquids
[ ] No added salt
[ ] No concentrated sweets
[ ] Low residue diet

Eating Locations
*No summary found*

Breakfast: [Select breakfast location...]
Lunch: [Select lunch location...]
Dinner: [Select dinner location...]

Beverage Preferences
*No summary found*
[ ] Prefers ice in beverages
[ ] Prefers water
[ ] Prefers apple juice

[ ] Prefers orange juice
[ ] Prefers cranberry juice
[ ] Prefers ginger ale

[ ] Prefers milk
[ ] Prefers coffee
[ ] Prefers tea

FIG. 17B

Medical Precautions

I want to... ▶

Cautions
*No summary found.*

Blood Pressure
☐ Resident had right mastectomy
☐ Resident had left mastectomy
☐ Resident had double mastectomy

Other
☐ Neuro Checks
☐ Has had recent surgery - check with nurse
☐ Seizure precautions - notify nurse

General Precautions
*No summary found.*

☐ Do not hospitalize
☐ No antibiotics
☐ Comfort measures only
☐ Has hospice care

Isolation Precautions
*No summary found.*

☐ Respiratory          ☐ C-diff contact
☐ Sputum contact       ☐ Stool contact
☐ Airborne             ☐ Droplet

VRE Contact
Select VRE contact... ▾

MRSA Contact
Select MRSA contact... ▾

FIG. 18

Mood/Behavior

I want to... ▼

Monitoring
*No summary found*
☐ Record mood
☐ Record behavior

Mood
*No summary found*

If resident displays loss of interest
☐ Encourage resident to socialize with other residents
☐ Focus on resident's strengths and past successes
☐ Provide tasks and activities specific to the resident's interests
☐ Reminisce with resident Add new intervention: [          ]

If resident displays sad, apathetic, or anxious appearance
☐ Approach the resident from the front
☐ Approach the resident in a calm, quiet manner
☐ Call the resident by name
☐ Help resident express feelings
☐ Offer snack or beverage
☐ Offer toileting
☐ Provide tasks and activities specific to the resident's interests
☐ Speak slowly
☐ Talk socially about non-care issues Add new intervention: [          ]

If resident displays sleep-cycle issues
☐ Encourage exercise and activity early in the day
☐ Follow bedtime rituals
☐ Keep noise level low
☐ Limit daytime naps
☐ Offer snack or beverage
☐ Offer toileting

FIG. 19A

Add new intervention:

If resident displays verbal expressions of distress
☐ Approach the resident from the front
☐ Approach the resident in a calm, quiet manner
☐ Call the resident by name
☐ Do not interrupt or rush the resident
☐ Give simple choices
☐ Speak slowly
☐ Use simple words and sentences Add new intervention:

Custom Notes: Mood
None available.
Add New Note

Expires:
○ Never
○ Date:

Behavior
No summary found!

If resident displays physically abusive behavior
☐ Approach the resident from the front
☐ Approach the resident in a calm, quiet manner
☐ Ask another caregiver to help with resident
☐ Call the resident by name
☐ Speak slowly and calmly Add new intervention:

FIG. 19B

If resident resists care
☐ Clearly explain care
☐ Consider having caregiver of different gender assist
☐ Give choice of times for care to be performed
☐ Leave resident and return later
☐ Provide opportunity for resident to make own choices
☐ Talk with resident about non-care issues before completing task Add new intervention: [    ]

If resident displays socially inappropriate/disruptive behavior
☐ Have resident return to room
☐ Offer snack or beverage
☐ Offer toileting
☐ Provide tasks and activities specific to the resident's interests
☐ Reassure resident
☐ Redirect resident Add new intervention: [    ]

If resident displays verbally abusive behavior
☐ Do not argue with resident
☐ Focus on subjects that are not upsetting
☐ Have resident return to room
☐ Leave resident and return later
☐ Redirect resident
☐ Speak calmly Add new intervention: [    ]

If resident wanders
☐ Accompany resident when leaving unit
☐ Offer snack or beverage
☐ Offer toileting
☐ Provide safe place for resident to wander
☐ Provide tasks and activities specific to the resident's interests Add new intervention: [    ]

FIG. 19C

Positioning

Physical Functioning
*No summary found.*

Self-performance: [Select self-performance...]
Level of support provided: [Select level of support...]

Cautions
*No summary found.*

☐ High risk for falls
☐ Balance problems

Avoid Pressure Ulcers
Keep off:
☐ Limit sitting out of bed to meals only
☐ Float heels to avoid pressure
  ☐ Left   ☐ Right   ☐ Back
  ☐ Heels
  ☐ Elbows
Avoid pressure:
  ☐ Back
  ☐ Neck   ☐ Upper extremities
          ☐ Lower extremities

Mobility
Foot drop:   ☐ Left  ☐ Right
Paralysis:   ☐ Left  ☐ Right
Weakness:   ☐ Left  ☐ Right
☐ Can wheel self
☐ Contracture
☐ Limited range of motion I want to... ▶

FIG. 20A

Hip and Joint Cautions
- ☐ Uses hip chair
- ☐ No bending hip past 90 degrees
- ☐ No twisting
- ☐ Keep knees apart
- ☐ No pigeon-toed position

Monitoring
*No summary found.*

Reposition resident:
Select time... ▸ AM/PM... ▸ Add another?
☐ Test and reapply bed or chair alarm

Multi-PODUS Boot
Apply/remove: ☐ Day ☐ Evening ☐ Night

Heel protector
Apply/remove: ☐ Day ☐ Evening ☐ Night

Special Equipment
*No summary found.*
- ☐ Pillows
- ☐ Bed cradle
- ☐ Air mattress
- ☐ Wheelchair
- ☐ Broda chair
- ☐ Recliner
- ☐ Trapeze
- ☐ Wedges
- ☐ Footboard
- ☐ Foot cradle
- ☐ Overlay mattress in bed Rails: Select rails to put up... ▸

Safety and Emergency
- ☐ Foot rests removed
- ☐ Uses perimeter mattress sleeve
- ☐ Put mat in place beside bed
- ☐ Ensure signal cord within reach at all times
- ☐ Half-privacy door

Bed Mobility
*No summary found.*
- ☐ Rolls
- ☐ Elevate head of bed
- ☐ Uses low bed

FIG. 20B

Transfers

I want to... ▶

Physical Functioning
*No summary found.*
Self-performance: [Select self-performance...]
Level of support provided: [Select level of support...]

Cautions
*No summary found.*

Pain cautions
- ☐ Head
- ☐ Neck
- ☐ Back
- ☐ Abdomen
- ☐ Ribs
- ☐ Wound
- ☐ General arthritic pain ☐ Left foot   ☐ Right foot
☐ Left leg    ☐ Right leg
☐ Left hip    ☐ Right hip
☐ Left arm    ☐ Right arm
☐ Left hand   ☐ Right hand

Monitoring
*No summary found.*
☐ Test and reapply bed or chair alarm

Special Equipment
*No summary found.*
- ☐ Cane
- ☐ Wheelchair
- ☐ Electric wheelchair or cart
- ☐ Gait belt
- ☐ Pivot disc
- ☐ Sliding board
- Rails: [Select rails to put up...]

Lift
- ☐ Standing lift
- ☐ Sling lift

Devices
- ☐ Lap tray
- ☐ Pummel cushion
- ☐ Grab bars

Walker
- ☐ Rolling walker
- ☐ Three-wheel walker
- ☐ Contact guard with walker
- ☐ Platform device on walker

FIG. 21

Vitals and Weight

I want to... ▶

Cautions
*No summary found*

☐ Do not take BP from right arm
☐ Do not take BP from left arm
☐ Do not take BP from either arm
☐ Use thigh for BP
Temperature location: [Select location... ▶]

Monitoring
*No summary found*

All Vitals

Starts: [____] [Select time... ▶] [AM/PM... ▶]
Repeats: [Does not repeat ▶]
Ends: ⦿ Never
○ Until

Blood Pressure

Starts: [____] [Select time... ▶] [AM/PM... ▶]
Repeats: [Does not repeat ▶]
Ends: ⦿ Never
○ Until

FIG. 22A

Pulse

Starts: [        ] [Select time...] [AM/PM...]
Repeats: [Does not repeat ▸]
Ends: ◉ Never
      ○ Until

Respiration

Starts: [        ] [Select time...] [AM/PM...]
Repeats: [Does not repeat ▸]
Ends: ◉ Never
      ○ Until

Temperature

Starts: [        ] [Select time...] [AM/PM...]
Repeats: [Does not repeat ▸]
Ends: ◉ Never
      ○ Until

Weight

Starts: [        ] [Select time...] [AM/PM...]
Repeats: [Does not repeat ▸]
Ends: ◉ Never
      ○ Until

FIG. 22B

VOICE ASSISTANT SYSTEM

CROSS-REFERENCE TO RELATED APPLICATION

This application claims the benefit of U.S. Provisional Application No. 61/087,082, entitled "VOICE ASSISTANT SYSTEM", filed Aug. 7, 2008, which application is incorporated herein by reference in its entirety.

FIELD OF THE INVENTION

This invention generally relates to the use of speech or voice technology in a work environment to facilitate a variety of tasks.

BACKGROUND OF THE INVENTION

Speech or voice technology, in the form of speech recognition, is used in a variety of different environments to facilitate the completion of work or various tasks. One example of a specific use for a voice-directed system is the direction of a worker to perform various tasks and to collect data associated with the task execution.

In a typical voice-directed work system, the worker wears a mobile computer having voice or speech capabilities. The computer is worn on the body of a user, such as at their waist, and a headset device connects to the mobile computer, such as with a cable or possibly in a wireless fashion. In another embodiment, the mobile computer might be implemented directly in the headset. The headset includes one or more speakers for playing voice instructions and other audio that are generated or synthesized by the mobile computer to direct the work of the user and to confirm the spoken words of the user. The headset also has a microphone for capturing the speech of the user to determine the commands spoken by the user and to allow the entry of data using the user's speech and speech recognition. Through the headset and speech recognition and text-to-speech capabilities of the mobile computer, workers are able to receive voice instructions or questions about their tasks, to receive information about their tasks, to ask and answer questions, to report the progress of their tasks, and to report various working conditions, for example.

The mobile and or wearable computers allow the users that wear or use them to maintain mobility at a worksite, while providing the users with desirable computing and data-processing functions. Generally, such mobile computers often provide a wireless communication link to a larger, more centralized computer system that directs the work activities of a user within a system and processes any user speech inputs, such as collected data, in order to facilitate the work. An overall integrated system may utilize a central system that runs a variety of programs, such as a prop-am for directing a plurality of mobile computers and their users in their day-to-day tasks. The users perform manual tasks and enter data according to voice instructions and information they receive from the central system, via the mobile computers. This process is generally referred to as voice-directed work as the user takes specific direction from the central system and their computer like they might take direction from a manager or supervisor or from reading a work order or to-do list.

The mobile computers provide a significant efficiency in the performance of a user's tasks. Specifically, using such mobile computers, the work is done virtually hands-free without equipment to Juggle or paperwork to carry around. However, while existing speech systems provide hands-free operations, voice-directed work may be overly structured for some users and for some work environments. Various work environments require that the worker know what they are doing in any particular task, and thus they do not have to be told how to specifically perform a particular task or what order to handle multiple tasks. Directing work in those environments in an automatic fashion, as is the case with typical voice-directed work, is not suitable and can be overbearing.

One such environment that requires greater worker flexibility is the work environment in a nursing home or, assisted living facility. In such facilities, nurses create care plans for all of the residents, and the care plans define the different tasks to be performed by the nurses or by certified nursing assistants ("CNAs") for the residents. In particular, each CNA, for example, has to be aware of and accountable for the tasks in the care plans of the residents that are assigned by the nurses to that CNA. Generally, the CNAs know how to perform the various tasks, such as bathing a resident, and do not need to be told by the central system how to perform the task. Furthermore, the CNA may also control the order in which they choose to address a multitude of tasks and thus take advantage of certain efficiencies in their workflow. The workflow will often depend upon the CNAs environment, their location, the urgency of the task and various other factors, and thus they have great flexibility in performing their work. For example, a CNA may want to first take the vitals of an assigned resident if the CNA has immediate access to the proper equipment for taking the vitals, and then bathe the resident. Or vice versa.

Therefore, the rigid approach of traditional voice-directed work environments, while suitable for some work, would not be suitable in a resident or patient care environment. In fact, the CNA is more likely to be hindered by a computer or device that rigidly directs the CNA to perform their tasks in a certain order or to ignore their own judgment with respect to an efficient workflow.

Furthermore, in traditional voice-directed work, the back and forth of the speech is usually constant as the worker is directed to a task, confirms completion of the task and then is immediately directed to the next task. The central system controls the dialog and thus, to some extent, controls the worker. As may be appreciated, in a patient or resident care facility, a CNA or other worker will often be speaking with the resident or other staff in the course of their day. As such, it would be disruptive to have to constantly be interfacing with an aggressive voice-directed system while also trying to converse with another person. Furthermore, many of the residents in such facilities are older and may find it disturbing and confusing when their CNA or other attendee has to speak at inappropriate times to maintain their workflow because the voice-directed system is controlling the dialog.

A need therefore exists in improving how a speech recognition system might facilitate a more efficient work environment without being overly rigid and overly domineering. There is further a need for a voice or speech system that can act to assist users with their work as the user needs it, rather than aggressively control the workflow and the speech dialog interface. Still further, in patient or resident care facilities, there is a need for efficient delivery of information and communications regarding the work tasks to increase efficiency and accuracy in the environment.

SUMMARY OF THE INVENTION

Embodiments of the invention provide for a method and apparatus to assist a user in the performance of a plurality of tasks. In one embodiment, the method comprises storing a care plan in a voice assistant carried by a user, the care plan defining a plurality of tasks to be performed by the user as part of a workflow. The method further comprises capturing speech input from the user with the voice assistant determining, from the speech input, a selected interaction with a care plan, and, in response to the selected interaction, providing a speech dialog with the user through the voice assistant that is reflective of the care plan.

Alternative embodiments of the invention provide for a method of assisting a user with a plurality of tasks that comprises capturing speech input of a user with a voice assistant and determining, from the captured speech input of the use, a first weight associated with a resident. The method further comprises associating the first weight with a care plan using the voice assistant, the care plan being associated with the resident, comparing the first weight to a second weight for the resident, the second weight associated with the resident and the care plan, and providing a speech dialog regarding reweighing the resident based on the comparison of the first weight and the second weight.

These and other advantages will be apparent in light of the following figures and detailed description.

BRIEF DESCRIPTION OF THE DRAWINGS

The accompanying drawings, which are incorporated in and constitute a pall of this specifications illustrate embodiments of the invention and, together with a general description of the invention given above and the detailed description of the embodiments given below, serve to explain the principles of the invention.

FIG. 2A-2B is an example of a care plan for a resident that may be generated via a nursing workstation in the voice assistant system of FIG. 1 consistent with the principles of the present invention;

FIG. 4 is one example of a document that may be physically carried by a user to interact with the voice assistant system of FIG. 1 consistent with the principles of the invention;

Figure 12:
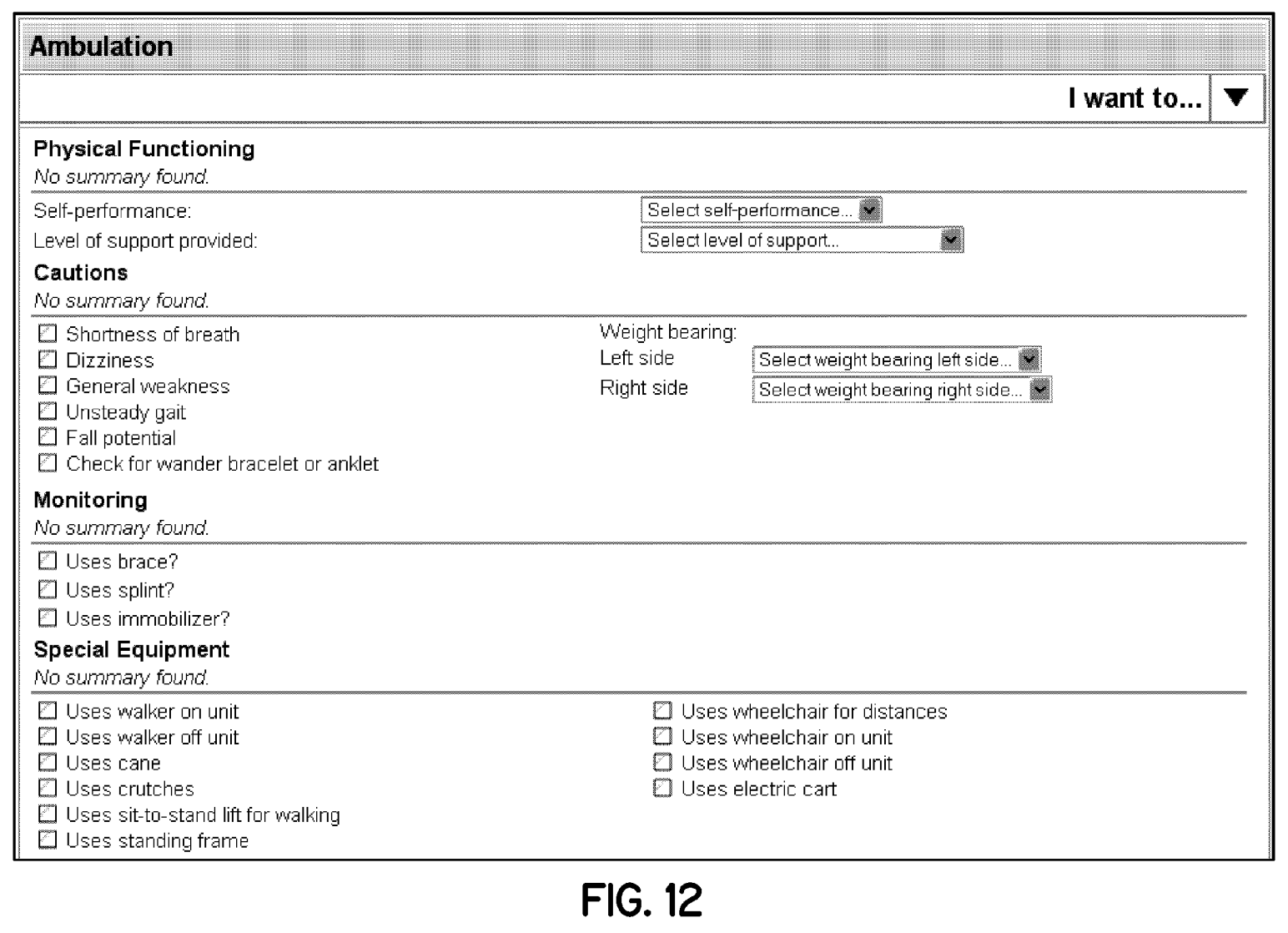

FIG. 12 is an example of another care plan for a resident similar to FIGS. 2A-2B;

FIGS. 13A-13B are examples of another care plan for a resident similar to FIGS. 2A-2B;

FIG. 14 is an example of another care plan for a resident similar to FIGS. 2A-2B;

FIG. 15 is an example of another care plan for a resident similar to FIGS. 2A-2B;

FIGS. 16A-16B are examples of another care plan for a resident similar to FIGS. 2A-2B;

FIGS. 17A-17B are examples of another care plan for a resident similar to FIGS. 2A-2B;

FIG. 18 is an example of another care plan for a resident similar to FIGS. 2A-2B;

FIGS. 19A-19B-19C are examples of another care plan for a resident similar to FIGS. 2A-2B;

FIGS. 20A-20B are examples of another care plan for a resident similar to FIGS. 2A-2B;

FIG. 21 is an example of another care plan for a resident similar to FIGS. 2A-2B; and FIGS. 22A-22B are examples of another care plan for a resident similar to FIGS. 2A-2B.

Figure 1A:
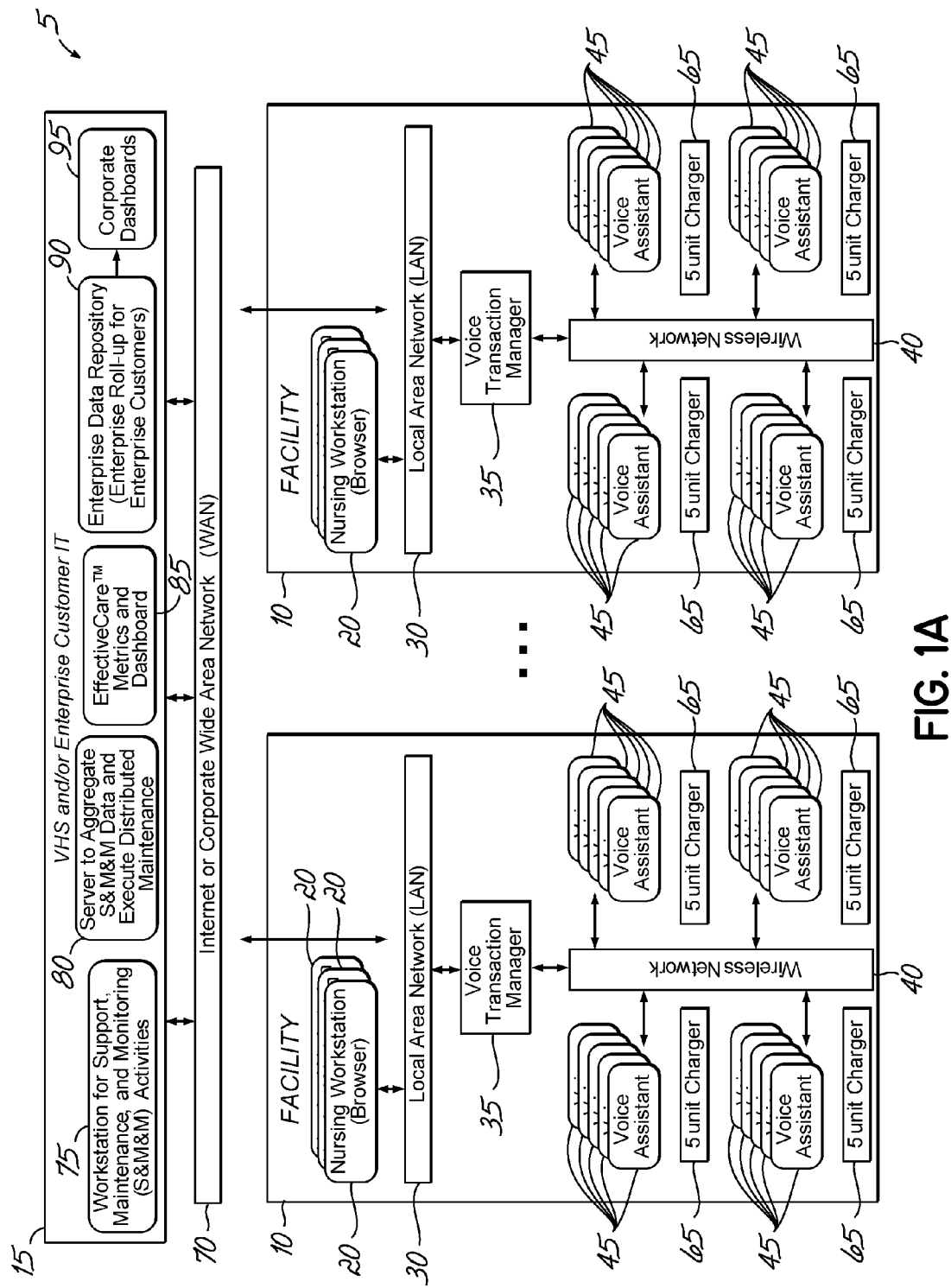
FIG. 1A is a block diagram of a distributed implementation of a voice assistant system consistent with the principles of the present invention.

It should be understood that the appended drawings are not necessarily to scale, presenting a somewhat simplified representation of various features illustrative of the basic principles of embodiments of the invention. The specific design features of embodiments of the invention as disclosed herein, including, for example, specific dimensions, orientations, locations, and shapes of various illustrated components, as well as specific sequences of operations (e.g., including concurrent and/or sequential operations), will be determined in part by the particular intended application and use environment. Certain features of the illustrated embodiments may have been enlarged or distorted relative to others to facilitate visualization and clear understanding.

DETAILED DESCRIPTION

Embodiments of the invention provide a voice assistant system for assisting a user. In some embodiments, the voice assistant assists a CNA or other care provider with performing a variety of tasks during the CNA's work shift. It is understood that the voice assistant system may be used in other work environments as well. Consistent with embodiments of the invention, the CNA may engage the inventive voice assistant via a main menu in the form of Situational Awareness Questions, and the CNA may be provided with a speech dialog that answers the various questions and/or provides other information. By doing so, the voice assistant system assists the CNA by providing information that is more pertinent to the situation the CNA is encountering, generally reducing the rigidity of voice-directed work. As will be readily understood, while a CNA is set forth herein as a particular person to utilize the present invention in a care facility, embodiments of the invention are not limited to a particular user. Alternative users of various embodiments of the invention are anticipated and understood to be beneficiaries of the features disclosed herein. For example, a physician, nurse, and/or other caregiver in a facility may use various embodiments of the invention.

The CNA may also use a speech command, and the CNA may be provided with a speech dialog associated with the command to assist the CNA with the execution of a task. Moreover, the voice assistant system may also analyze data received from the CNA and provide a speech dialog at the point of care that may assist the CNA in the efficiency and accuracy of their work. Furthermore, the voice assistant system may provide reminders, pages and/or other indications (e.g., "all clear" indications or messages) to assist the CNA in managing their workflow. In one embodiment, the voice assistant system may be and/or may incorporate or include the AccuNurse® software and/or hardware offered by the assignee of this application, Vocollect Healthcare Systems, Inc. ("VHS") of Pittsburgh, Pa.

Those of ordinary skill in the art will appreciate that the voice assistant system described herein seeks to assist the CNAs with their tasks in a more flexible and fluid manner by providing audible tones, messages regarding instructions, information in response to the Situational Awareness Questions, and/or assistance with execution of the tasks and analysis of data via the commands, as opposed to rigid, conventional voice-directed systems that order users to perform specific tasks in a set order, set flow, set manner, and/or at a set time. Indeed, voice-directed work typically dictates each task to be performed, the order they are performed in, and when they are to be performed, whereas the voice assistant system described herein allows a CNA to decide what tasks to perform, the order to perform them, and when to perform them, with care plans providing guidance. As such, the voice assistant complements the CNA's task choices and provides assistance via a voice dialog as needed to the CNA (e.g., when the CNA initiates the assistance, when the CNA should be informed of something such as a page). In other words, in conventional voice-directed work systems, the system is typically in charge and the users follow the orders, whereas in a voice assistant system the CNA is in charge and the system follows orders to provide assistance as needed.

Turning now to the Drawings, wherein like numbers denote like parts throughout the several figures, FIG. 1A is a diagrammatic illustration of a voice assistant system 5 that may be in the form of a distributed computing system, with computing activities associated with at least one onsite nursing home or assisted living facility as at 10. The nurses, CNAs, and residents of a facility are typically physically located at the facility 10, while centralized support and management capabilities for the voice assistant system 5 may be provided by an offsite VHS department and or by an onsite enterprise customer IT department 15.

As illustrated, the voice assistant system 5 may include more than one facility 10, and each facility 10 may be subdivided into a plurality of units. All of the units may be referred to as a site, but will generally be referred to as the facility 10 for simplicity, unless otherwise stated. Also for simplicity, the discussion will primarily focus on a single facility 10 and its respective nursing workstation 20, voice assistant 45, and charger 65 (discussed farther hereinbelow), even though a plurality of these items are illustrated in FIG. 1. Those of ordinary skill in the art will appreciate, however, that embodiments of the invention may apply equally to the other facilities (including other nursing workstations, other voice assistants, and other chargers) in the voice assistant system 5. Furthermore, the discussion of embodiments of the invention will be from the perspective of a single CNA utilizing the voice assistant 45 for simplicity, but those of ordinary skill in the art will appreciate that each CNA and/or each nurse may have a voice assistant 45.

Turning to the facility 10, at least one care plan is generated by a nurse or other qualified personnel for each resident at the facility 10. In one feature of the present invention, interactive care plans are created and maintained for interacting with the voice assistant 45. As such, the care plans may be accessible through the nursing work station 20. The information of the care plans may be accessed by the voice assistants 45 to assist the CNAs, by voice, in the various tasks associated with the care plans. Advantageously, it is believed that this is a significant improvement over the use of written care plans that are typically located in various binders at a nursing station. It is worth noting that the CNAs may not be authorized to generate and/or change care plans, but the CNAs can view and perform the tasks in the care plans. To generate and/or revise care plans, the facility 10 may include at least one nursing workstation 20, and a nurse or other qualified personnel associated therewith may generate and/or revise a care plan as needed via a graphical user interface, such as an application displayed via a web browser, associated with the nursing workstation 20 (see FIG. 1B). Specifically, the application displayed may display a variety of information for the nurse to select, including pull-down, menus, boxes, etc. Using the pull-down menus, boxes, etc., the nurse may generate and/or revise a care plan as needed. FIGS. 2A and 2B illustrate an exemplary care plan 25 for toileting for a resident named Jane Doe as displayed in the application. Specifically, FIGS. 2A and 2B illustrate an exemplary care plan 25 prior to a nurse saving the changes to the toileting care plan. Various other care plans may exist as well. For example, the care plan of FIG. 12 is directed to Ambulation of the Resident; FIGS. 13A-13B to Background Information; FIG. 14 is directed to Bathing; FIG. 15 to Dressing; FIGS. 16A-16B to Personal Hygiene, FIGS. 17A-17B to Meals; FIG. 18 to Medical Precautions; FIGS. 19A-19C to Mood/Behavior; FIGS. 20A-20B to Positioning, FIG. 21 to Transfers; and FIGS. 22A-22B to Vitals and Weight. However, one of ordinary skill in the art will appreciate that there may be additional care plans for other tasks and/or information. Each care plan may have various menus, boxes, and other selectable fields for entering or selecting information and parameters for the care plan. The care plans may be displayed via the application in the web browser, and the care plans may direct the workflow of the CNA via the voice assistant 45 (discussed further hereinbelow). The care plans for a particular resident may determine what tasks the CNA must perform for that resident during the shift.

Furthermore, the nursing workstation 20 may also be utilized to generate and/or update work assignments for the CNAs. For example, before the start of the shift of a particular CNA, the nurse or other qualified personnel in the facility 10 (or unit thereof) may set tip and/or update the work assignment for the CNA via the nursing workstation 20. As such, the nurse or qualified personnel may set up and/or update a work assignment for the CNA to include an assignment of residents to that CNA for a shift or appointments associated with the CNA (including an appointment with a resident), as well as make changes to a care plan for a resident. The nurse or other qualified personnel may also print out an exception report from the nursing workstation 20 that indicates the tasks that still need to be performed by a CNA.

The nursing workstation 20 may represent practically any type of computer, computer system, appliance, or other programmable electronic device. The nursing workstation 20 may also be capable of functioning as a client and/or server or may be implemented using one or more networked computers, e.g., in a cluster or other distributed computing system. In some embodiments, the nursing workstation 20 may be similar to a client computer.

Along with the web browser, the nursing workstation 20 may also include an operating system, at least one processor such as a central processing unit (CPU), a memory, mass storage, a user interface, a network interface, and/or routines that are configured to be executed to implement the embodiments of the invention, whether implemented as part of an operating system or a specific application, component, program, object, module or sequence of instructions, or even a subset thereof, which will be referred to herein as "computer program code", or simply "program code." Program code typically comprises one or more instructions that are resident at various times in various memory and storage devices in a computer, and that, when read and executed by one or more processors in a computer, cause that computer to perform the steps necessary to execute steps or elements embodying the various aspects of the invention.

The information associated with at least one care plan may be transmitted (e.g., in digital form) from the nursing workstation 20 (e.g., using the network interface) via a local area network (LAN) 30 to a voice transaction manager 35. Each facility 10 may have at least one voice transaction manager 35 to store the care plans and facility configuration information. Specifically, the voice transaction manager 35 may represent and/or include practically any networked appliance, device, or computer as described hereinabove in connection with the nursing workstation 25. As such, and in some embodiments, the voice transaction manager 35 may include a web server and/or a database server as is known to a person of ordinary skill in the art. Thus, the voice transaction manager 35 may include at least one database for storing the data, which may in turn be transmitted from the voice transaction manager 35 to the nursing workstation 20.

Furthermore, in one embodiment of the invention, Solaris may be utilized as the native operating system in the voice transaction manager 35, but no explicit operating system dependencies may be required for the web server and/or the database server. Java may be utilized as the native programming language of the voice transaction manager 35, and the voice transaction manager 35 may be implemented and managed using conventional Internet technologies. The voice transaction manager 35 may also function as backup in case of data loss. From the perspective of the nurses and CNAs, the voice transaction manager 35 may not require onsite IT maintenance beyond turning the power on and off Furthermore, a type of network other than the LAN 30 may alternatively be utilized to transmit data from the nursing workstation 20 to the voice transaction manager 35.

Next, the information and data associated with at least one of the care plans in the voice transaction manager 35 may be transmitted (e.g., in digital form) from the voice transaction manager 35 (e.g., using the network interface) via wireless network 40 (e.g., a wireless local area network, or "WLAN") to at least one voice assistant 45. Data may also be transmitted from the voice assistant 45 to the voice transaction manager 35, for example, for storage and/or processing at the voice transaction manager 35.

The voice assistant 45 may include three separate portions, including a headset portion (e.g., including a microphone, one or more earpieces, and one or more speakers), a device portion and a connecting portion. In some embodiments, the connecting portion may be a cable or a wireless link.

Figure 3:
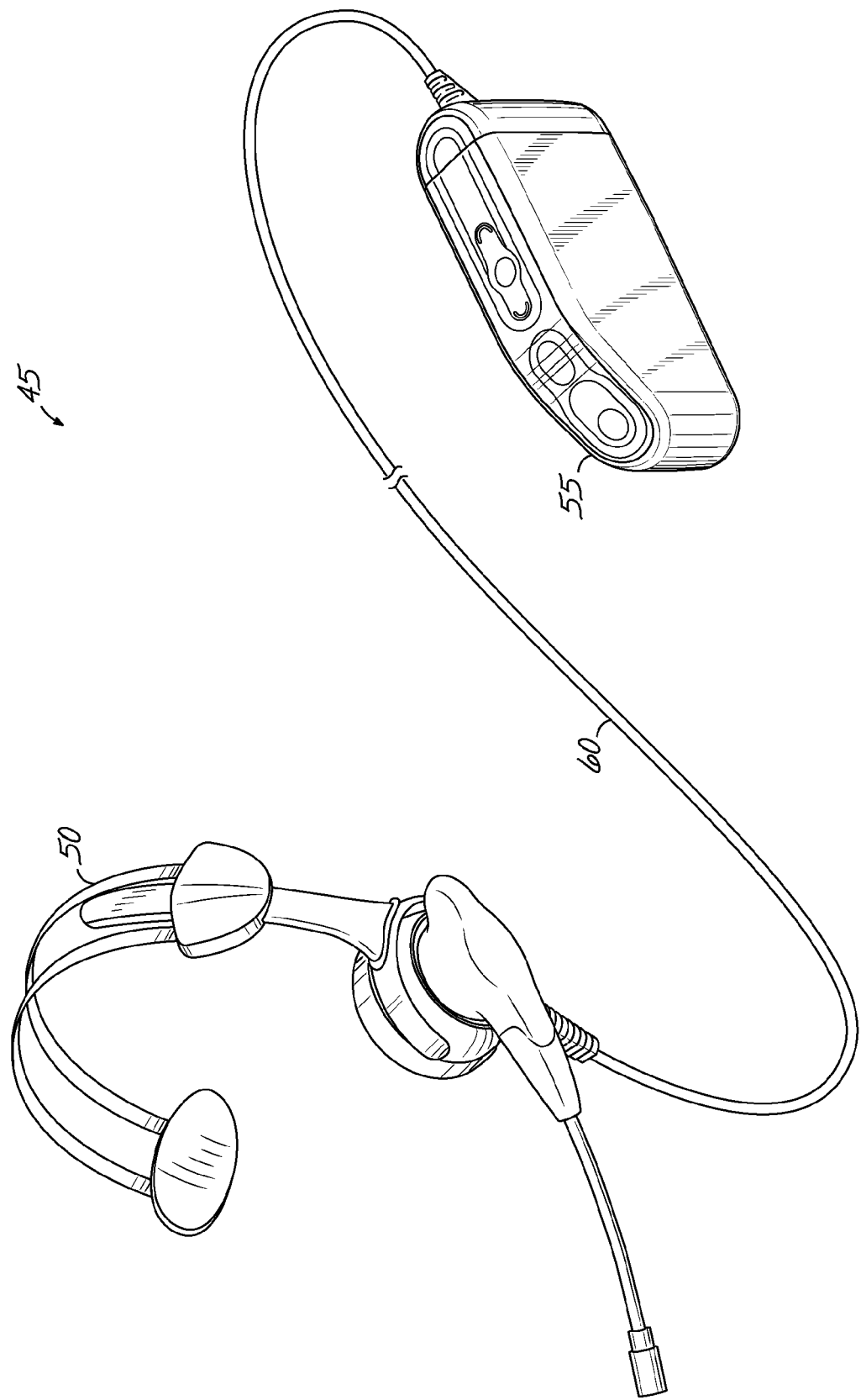
FIG. 3 is a side perspective view of one embodiment of a voice assistant of the voice assistant system of FIG. 1 consistent with the principles of the present invention.

Although the voice assistant 45 shown throughout the Figures has multiple different portions, the voice assistant 45 may represent and/or include practically any networked appliance, device, or computer as described hereinabove. An exemplary voice assistant 45 with a headset portion (or "headset") 50, a device portion (or "portable computer portion") 55, and a connecting portion such as a cable 60 that couples the headset portion 50 to the device portion 55 is illustrated in FIG. 3. In alternative embodiments, the headset 50 is coupled to the device portion 55 through a wireless link, which may also be referred to as a "connecting portion." In a further alternative embodiment the functionality of the device portion 55 may be incorporated into the headset 50 such that voice assistant 45 is one self-contained piece of equipment.

The voice assistant 45 may also include at least one database to store data received from the voice transaction manager 35. Furthermore, Situational Awareness Questions, as discussed below, may be answered by speech dialog utilizing the data in the database, and the data in the database may also be utilized to generate a speech dialog for certain commands (e.g., a "Review" command) and to store data from the user with respect to other commands (e.g., a "Document" command). The speech dialog may include at least one statement generated by the voice assistant 45.

In some embodiments, the voice assistant 45 is a wearable computer and/or a personal digital assistant (PDA) that includes WLAN capabilities. Alternatively, the voice assistant 45 may be a voice appliance that is deployed to perform specific functions for the CNA via a main menu associated with the voice assistant 45, instead of being deployed for a general purpose. In particular, the voice assistant 45 may be a client, and more specifically a "thick client" that is configured to perform speech recognition and speech synthesis. As such, and in some embodiments, the voice assistant 45 may be similar to a client computer.

In accordance with the principles of embodiments of the invention, each CNA at the facility 10 may have their own voice assistant 45 that they wear or carry. When a CNA connects the headset portion 50 to the device portion 55 via the connecting portion 60, or when a CNA turns the voice assistant 45 on, this may activate the voice assistant 45 and "log" the CNA on to the voice assistant system 5 (e.g., establish a connection between the voice assistant 45 and the nursing workstation 20 and/or voice transaction manager 35, as well as determine which particular CNA is logging onto the voice assistant system 5 based on an identification associated with the CNA and/or the voice assistant 45, and retrieve data associated with that particular CNA and/or voice assistant 45). In response to logging the CNA on to the voice assistant system 5, one or moose items may be transferred from the voice transaction manager 35 to the voice assistant 45. These items may include the list of residents assigned to the CNA for the shift, the care plan data for all of the residents assigned to the CNA, the appropriate voice templates and/or the facility configuration information, such as, but not limited to, the list of CNAs generally assigned or logged into the current shift. Moreover, the CNA may physically carry a document (e.g., document 62 illustrated in FIG. 4) that sets forth the speech vocabulary to interact with the voice assistant 45 (e.g., including the main menu 63 illustrated in FIG. 5). In particular, the CNA may use the voice assistant 45 to interact with the main menu by selecting from the predefined parameters in the form of speech input (e.g., including Situational Awareness Questions, commands and/or other vocabulary, at least a portion of which is illustrated on the document 62). The speech recognition capabilities of the voice assistant 45 receives the speech input and utilizes the speech recognition capabilities to convent the speech input into machine readable input (e.g., data that can be processed by the voice assistant 45 or another potion of the voice assistant system 5, including the nursing workstation 20 and/or voice transaction manager 35, for example). The speech synthesis capabilities of the voice assistant 45 may then provide speech dialog in response to the speech input (e.g., answers to a Situational Awareness Question and/or speech dialog in response to a command and/or other vocabulary, for example). Furthermore, the voice assistant 45 may also be utilized to provide the CNA with audible tones and/or speech dialog in response to various statuses. The main menu and voice user interface (VUI) will be discussed hereinbelow in connection with FIGS. 5-11.

Although one of ordinary skill in the art will appreciate that the voice assistant 45 may be implemented in a variety of ways (e.g., in some embodiments the voice assistant 45 includes only a headset 50 that in turn includes the functionality of the device portion 55), and one of ordinary skill will further realize that activation of the voice assistant 45 may cause transmission of the data from the voice transaction manager 35 to that voice assistant 45, it may be advantageous to utilize a thick client model and configure speech recognition and speech synthesis capabilities in the voice assistant 45. By doing so, the voice assistant 45 may avoid placing substantial amounts of network traffic on the wireless network (e.g., WLAN) 40, LAN 30, or WAN 70 (discussed hereinbelow in connection with area 15) during documentation or other activities.

Furthermore, in the thick client model, aside from downloading the care plans from the voice transaction manager 35 to the voice assistant 45 at the start of the CNA's shift, the CNA may continue to work and document independent of whether she or he has a network connection. For instance, once this data transfer is complete, the voice assistant 45 may support documentation for the entire shift, even in the absence of a working wireless network 40. As such, it may be advantageous to configure more processing and/or bandwidth intensive activities of the voice assistant 45 (e.g.; the speech recognition, processing and or speech synthesis capabilities) closer to the end users.

However, in the presence of an available network, the voice assistant 45 may receive updates, including real-time updates and near real-time updates (e.g., updates to care plans). Moreover, some or all of the speech input spoken by the CNA (e.g., speech input in response to a speech dialog or, alternatively, specific speech input not otherwise spoken in response to speech dialog) may be captured and transmitted (e.g., to the voice transaction manager 35) in real-time, near real-time and or in a delayed manner (e.g., at the end of shift, day, and/or after a predetermined period of time) in the presence of an available network. Indeed, it is also worth noting that the voice assistant 45 may support real time paging. For example, a page may be first sent to the voice transaction manager 35 and then relayed to its final destination(s). In an alternative embodiment, voice assistants 45 may be configured communicate with each other directly via the wireless network 40 to send a page.

It is worth noting that the care plans for the residents typically remain stable from day to day and from shift to shift. For example, a resident needs to eat meals every day, go to the bathroom every day, etc. A care plan may change if the nurse makes the change at the nursing workstation 20, as the CNA cannot change the care plans on his or her voice assistant 45, as discussed above. As such, care plans may be received by the voice assistant 45 at the start of every shift and/or upon activation to reflect any changes to the care plans that occurred prior to the start of the shift and/or activation, and the care plans may be dynamically maintained throughout the shift and/or activation to include any changes.

As the CNA completes the different tasks associated with the items in the care plans, a data set reflective of the work completed by the CNA may be generated at the voice assistant 45. The data set may be utilized for various purposes. For example, the data set may be utilized to answer the Situational Awareness Questions of the CNA (e.g., the answer may be based on the data set alone or the answer may be based on the data set and the care plans), to generate a historical report, to generate an MDS, and/or to generate an exception report (e.g., at the nursing workstation), among other purposes. Thus, the care plans on the voice assistant 45 are not configured to track the completed tasks or changes in response to the completion of work by the CNA. Rather, it is the generated data set that tracks completed work. Indeed, a new data set may be generated during each shift.

Figure 1B:
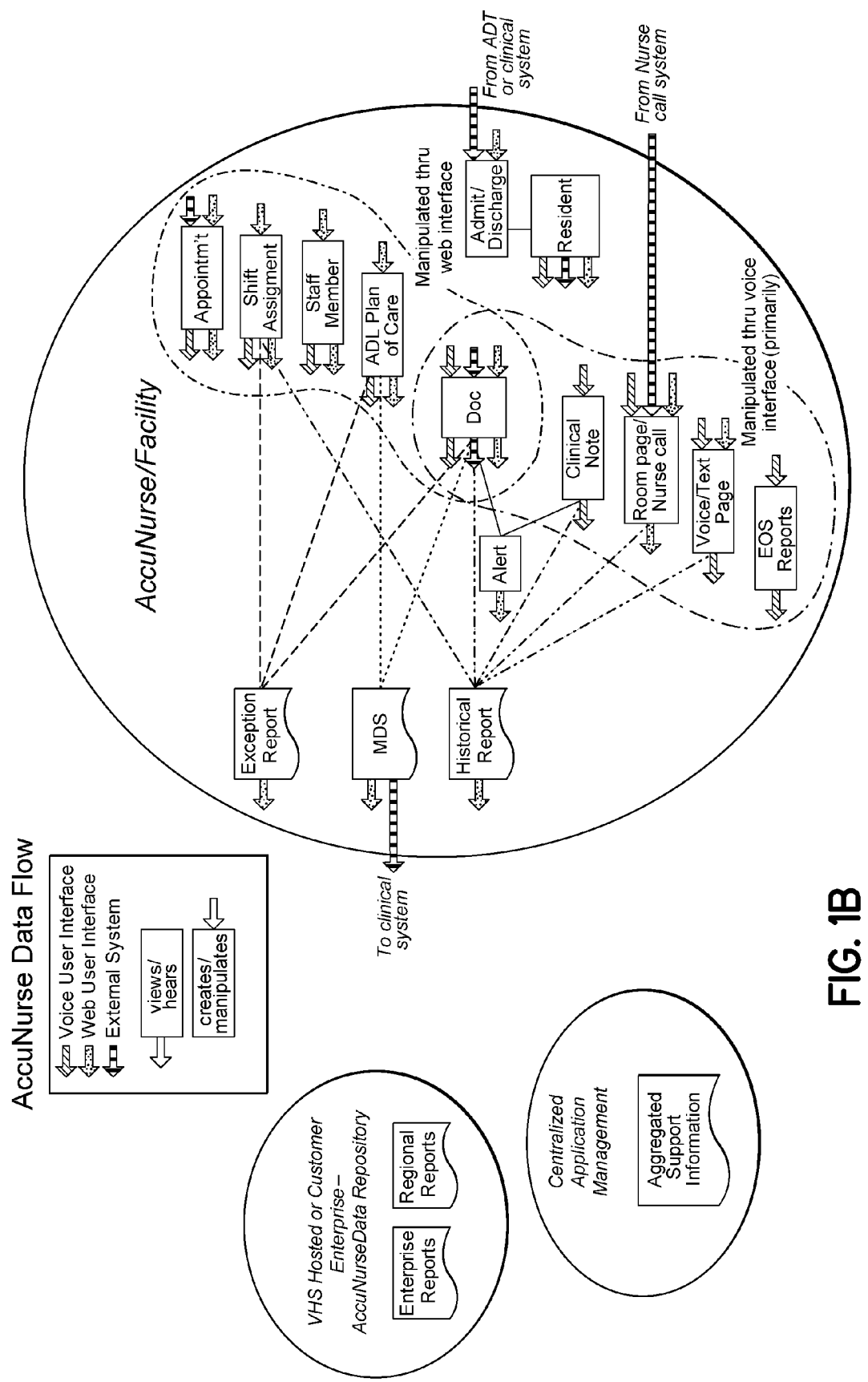
FIG. 1B is a block diagram of data flow in the voice assistant system of FIG. 1 consistent with the principles of the present invention.

FIG. 1B illustrates an exemplary overview of the data flow throughout the voice assistant system 5, including the care plans, pages, etc. Key attributes of the data flow in the voice assistant system 5 at the facility level may include the external interfaces (e.g., to ADT, MDS and/or nurse call systems), data that is primarily manipulated through the web interfaces (e.g., a web browser at the nursing workstation 20), data that is primarily manipulated through the voice interface (e.g., the voice assistant 45, main menu 63 and/or VUI), key reports (e.g., MDS, exception reports, and/or historical reports), and/or the plan of care documentation ("Doc" in the drawing). In particular, the "Doc" illustrates the overlap between the web interface and the voice interface.

Referring back to FIG. 1A, the facility 10 may also include at least one charger 65 to charge the voice assistant 45. As illustrated in FIG. 1A, each charger 65 may charge up to five voice assistants 45. Furthermore, a least one item in the facility 10 may transmit and/or receive data via the Internet or a corporate wide area network (WAN) 70 to the offsite Vocollect Healthcare Systems, Inc. department and/or the onsite enterprise customer IT department 15.

The offsite VHS department and/or the onsite enterprise customer IT department 15 may include a workstation for support, maintenance and monitoring (S&M&M) activities 75 as well as a server to aggregate S&M&M data and execute distributed maintenance 80. The offsite VHS department and/or the onsite enterprise customer IT department 15 may further include metrics and at least one dashboard 85 such as EffectiveCare™ offered by VHS, an enterprise data repository that may be utilized for enterprise roll-up for enterprise customers 90 and/or at least one corporate dashboard 95. For example, the offsite VHS department may be able to remotely maintain the voice transaction manger 35, provide other remote support, and/or monitor performance of the voice assistant system 5.

In short, the voice assistant system 5 may emphasize distributed execution, but centralized platform management and data roll-up, as discussed hereinabove. Moreover, those of ordinary skill in the art will readily appreciate that other functionality may be possible as well. Those skilled in the all will recognize that the exemplary environments illustrated in FIGS. 1A-1B, 2A-2B and 3-4 are not intended to limit the present invention. Indeed, those skilled in the art will recognize that other alternative hardware and/or software environments may be used without departing from the scope of the present disclosure.

Figure 5:
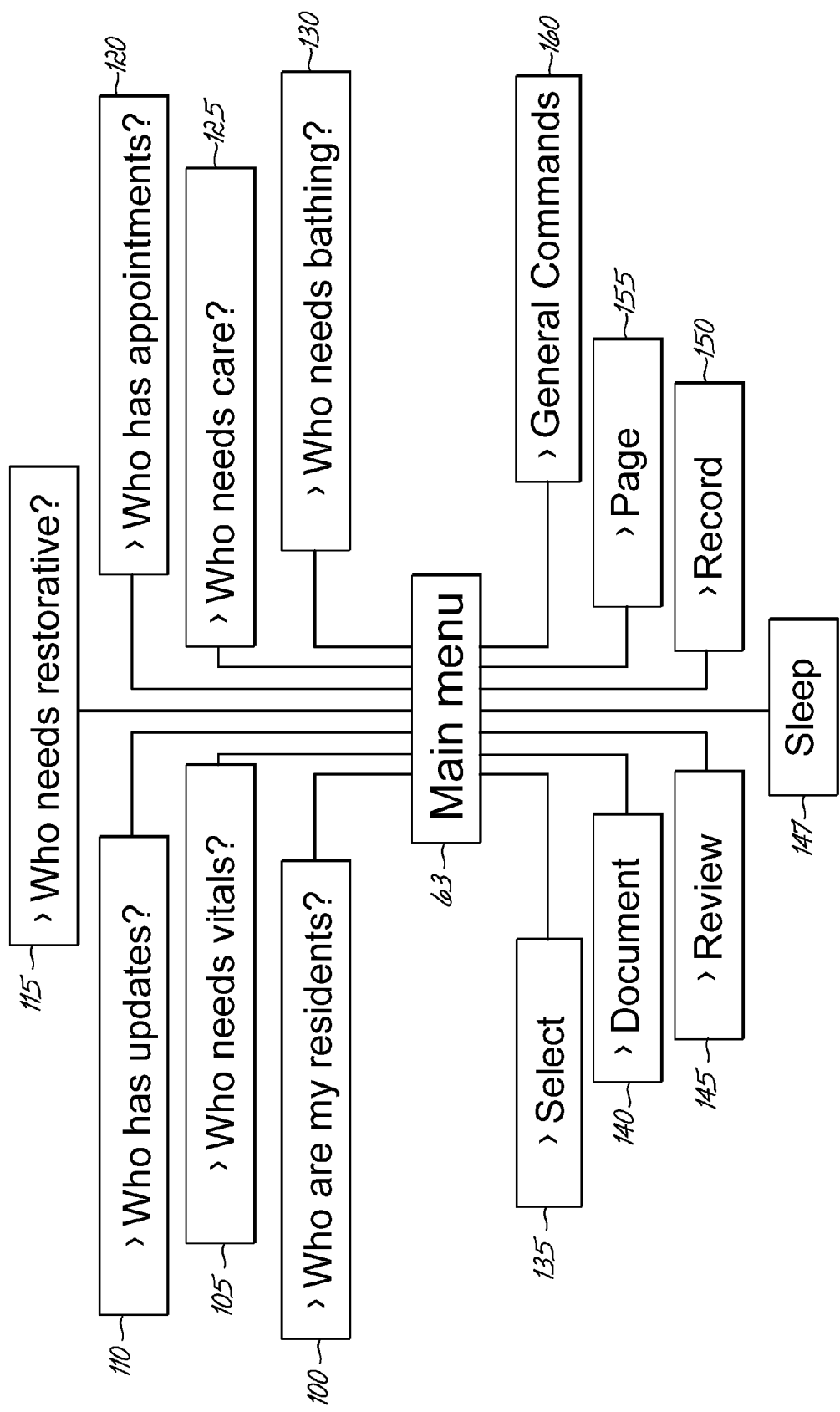
FIG. 5 is one embodiment of a main menu that a user may interact with, including selectable parameters in the form of questions and commands that the user may choose via the voice assistant of FIG. 3, consistent with the principles of the present invention.

Turning now to FIG. 5, via the main menu 63, the CNA may select at least one parameter through speech input that corresponds to a Situational Awareness Question and/or command. The speech recognition capabilities of the voice assistant 45 are utilized to receive the speech input of the user and determine the parameter selected by the CNA. A Situational Awareness Question may be utilized to query about certain situations often encountered by CNAs in their work shift such that the CNA may control their workflow with respect to various situations. For example, when a CNA faces a particular situation or is placed in a particular context, the CNA may be able to interact with the voice assistant 45 through a corresponding question and begin a speech dialog that answers the question based upon the available information. In other words, information that the CNA may need to be aware of, should be aware of, and/or needs while performing their tasks may be organized according to Situational Awareness Questions. For example, the situation or context may be related to the remaining work, time of shift (commencement of the shift, end of the shift, etc.), time of day (lunch time, snack time, etc.), current task or tasks (bathing, vitals, etc.), a particular resident the CNA is working with, a location in a facility, etc.

Various Situational Awareness Questions are illustrated as interrogatories 100-130 in FIG. 5 consistent with one embodiment of the invention. Respectively, these are, "Who are my residents?" (block 100), "Who needs vitals?" (block 105), "Who has updates?" (block 110), "Who needs restorative?" (block 115), "Who has appointments?" (block 120), "Who needs care?" (block 125), and "Who needs bathing?" (block 130). As such, these Situational Awareness Questions concern interrogatories associated with the identity of residents associated with a CNA, the identity of residents associated with a CNA that need their vitals recorded, the identity of residents associated with a CNA who have had updates made to their respective care plan, the identity of residents associated with a CNA who need one or more restorative programs, the identity of residents associated with a CNA who are in turn associated with appointments for care or other activities, the identity of residents associated with a CNA who currently need some sort of care, and the identity of residents associated with a CNA who currently need bathing. A restorative program, or restorative care, refers to activities that may help improve a resident's mobility, eating, muscle function, and the like that may be performed by a CNA. Those of ordinary skill in the ant will appreciate, however, that other Situational Awareness Questions may be supported as well by the invention, for example, "What's important?", "What's different?", or "What's changed?", "What's left?", "What's scheduled?", "Who's assigned?", "What is last shift report?", among others. As such, embodiments of the invention are not limited to the specific Situational Awareness Questions and interrogatories discussed herein.

In some embodiments, the answer to each Situational Awareness Question is provided by way of a speech dialog generated by the speech recognition and synthesis capabilities of the voice assistant 45, with the answer based upon care plan information and/or other information accessed and received by the voice assistant 45. In general, the speech dialog answering the "Who" related questions will provide the names and/or room numbers of the residents that satisfy the question. In some instances, the answer may be based upon information from some or all of the care plans associated with the voice assistant 45. Furthermore, the answer may be based upon, or take into account, tasks that have already been completed. For example, if the CNA wants to know, "Who needs bathing?", it may be advantageous for the speech dialog to inform the CNA of the assigned residents that still need bathing, and not inform the CNA of assigned residents that have already been bathed by the CNA (or assigned a task that has already been completed by another CNA). As such, the answer may reflect the completion of a task by the assigned CNA or even completion of a task by another CNA, as tracked by the voice assistant system 5. For example, the CNA might ask, "Who needs care?" The voice assistant 45 may then provide a list of the residents for whom various tasks still remain. Then, through other commands, and as discussed below, the CNA may select and review the tasks for a particular resident. That is, if the answer to a Situational Awareness Question listed Mr. Smith of Room 312 as needing care (e.g., in response to the interrogatory "Who needs care?") or some specific task (e.g., in response to the interrogatory "Who needs vitals?"), the CNA may use the select command 135 to select Mr. Smith and the review command 145 to obtain information about Mr. Smith. For example, "Review vitals" may be spoken by the CNA to obtain care plan in formation about vitals for Mr. Smith. In some embodiments, when the CNA begins to assist an unassigned resident, the care plan for that unassigned resident is sent to the voice assistant 45.

Similarly, the answers to any questions, such as, "Who has updates?" may be based upon information associated with a particular resident that has changed and/or information associated with one or more care plans that has changed since the CNAs last login. Changes may occur because of an action by a nurse at the nursing station 20 during the CNA's shift, because of a change in the care plan of an assigned resident, because of an assignment of another resident to the CNA, etc. Moreover, there may be updates as to the facility configuration data, such as the number of CNAs currently working or logged on. As noted above in connection with FIG. 1A, updates may be sent from the nursing workstation 20 to the voice transaction manager 35 and/or to the voice assistant 45 during a shift. As such, the care plans may be dynamically maintained. Upon noting a resident with updates, the CNA can select the resident, and speak or issue a "Review updates" command for that resident.

In general, the commands may be associated with various tasks and invoked by the CNAs for assistance with, and for execution of, pending tasks. Various exemplary commands are illustrated as commands 135-160 in FIG. 5. Respectively, these are "Select" (block 135), "Document" (block 140), "Review" (block 145), "Sleep" (block 147) "Record" (block 150), "Page" (block 155) and General Commands (block 160). Furthermore, each of these commands may have additional sub-commands and/or sub-categories associated with them. For example, the "Review" command may have a sub-category for "toileting" to review the toileting of a resident. Similarly, the "Document" command may have a sub-command for "meals," the "Page" command may have a sub-command for "unit," etc. However, those of ordinary skill in the art will appreciate that additional commands other than those listed may also be supported.

For at least some commands, speech dialog is provided that corresponds to that command. The speech dialog may include asking the user to speak at least one input, repeating the CNAs input, etc. The speech dialog may be based upon the data in the voice assistant 45, including the care plans and/or voice templates. Such dialogs may be generated by the voice transaction manager 35 and/or the voice assistant 45 using speech synthesis as is known to a person of ordinary skill in the art. The text of the speech dialog may depend on the specific command and the data requested by the voice assistant 45, or the information to be provided by the voice assistant 45. As may be appreciated, the speech dialog could take various different forms to provide information about a resident or a care plan to a CNA, or to obtain information and data about a resident pursuant to their care plan. Thus, the invention is not limited to the specific questions or format of any given speech dialog.

Figure 6:
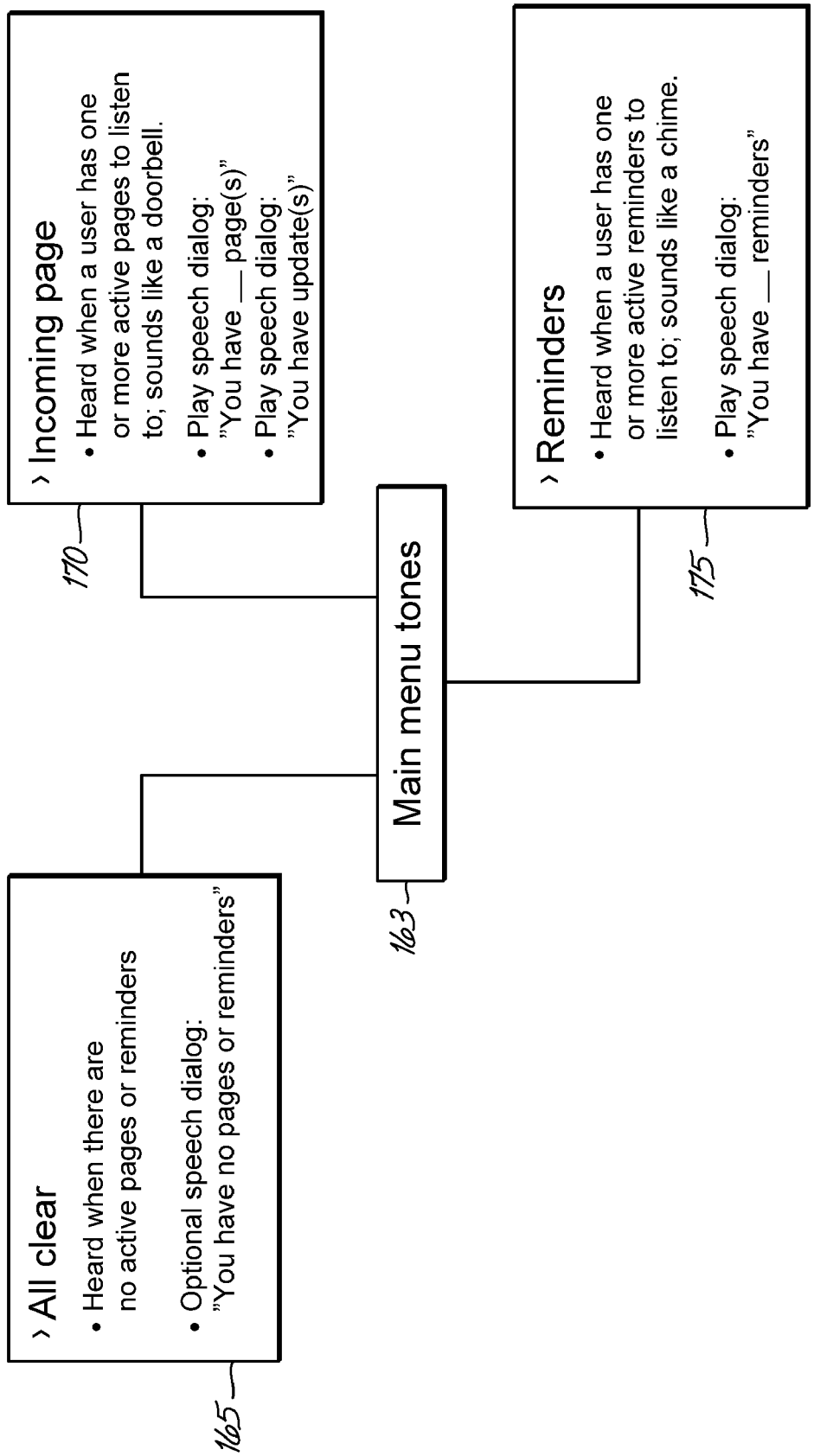
FIG. 6 is the main menu of FIG. 5, including tones that may be provided to the user, consistent with the principles of the present invention.

In addition to providing speech dialog in response to Situational Awareness Questions and or commands, the voice assistant 45 may also provide a CNA with a variety of audible tones, or audible speech tones 163, as well as speech dialog in response to various statuses, as illustrated in FIG. 6. In some embodiments, such as in response to a status change (e.g., a new page and/or reminder) while the user is at the main menu, in response to a user navigating to the main menu while a page and/or reminder is outstanding (e.g., unaddressed) and/or in response to a predetermined time period elapsing while a voice assistant 45 is in the sleep mode with a page and/or reminder outstanding, an audible tone and a speech dialog associated therewith is provided, followed by another audible tone. When the CNA is not at the main menu, such as when the CNA is reviewing or documenting information, all audible tone may be provided without either the speech dialog associated therewith or the second audible tone in response to a status change. For example, an "all clear" tone 165 may be provided when there are no active pages or reminders. The "all clear" tone 165 may be followed by speech dialog that indicates "You have no pages or reminders," and that speech dialog may be followed by another "all clear" tone 165. The "incoming page" tone 170 may be provided when the CNA has one or more active pages to listen to, and may sound like a doorbell. The "incoming page" tone 170 may be followed by speech dialog that indicates "You have {N} pages," wherein "N" is the number of pages for that CNA, and that speech dialog may be followed by another "incoming page" tone 170. The incoming page may be from another CNA and may include a recorded voice message similar to a conventional voicemail. However, the page is a silent page in that a public address system (i.e., PA system) need not be utilized, leading to less disruption.

Moreover, a "reminder" tone 175 may be provided when the CNA has one or more active reminders to listen to, and may sound like a chime. The "reminder" tone 175 may be followed by speech dialog that indicates "You have {M.} reminders," wherein "M." is the number of reminders for that CNA, and that speech dialog may be followed by another "reminder" tone 175. A reminder may be based upon the care plans of the assigned residents. For example, a specific task in a care plan may have to be completed at a certain time or by a certain time (e.g., preparation for an appointment), and the reminder tone 175 may be provided to the CNA to make them aware that the time has arrived or is approaching.

The audible tones and/or speech dialogs associated therewith provide audible indications to the CNA of particular information that needs attention. Therefore, rather than acting as a visual icon regarding that information., such audible tones and/or speech dialogs operate as an "earcon" to indicate to the CNA that something needs attention. Generally, a reminder earcon will be associated with time-sensitive information, such as a resident appointment that is within the care plan of a particular resident, or a time for a particular task within the care plan of that resident. For example, if a certain resident needs toileting at a particular time, a reminder earcon may be triggered to remind the CNA of the time-sensitive task. Again, the reminder earcon may include the reminder tone 175, followed by a speech dialog associated therewith, and then followed by another reminder tone 175 in response to a reminder status change while the user is at the main menu, in response to a user navigating to the main menu while there is a reminder outstanding, and/or in response to a predetermined time period elapsing while a voice assistant 45 is in the sleep mode and there is a reminder outstanding. Alternatively, the reminder earcon may include only the reminder tone 175 in response to a reminder status change when the CIA is not at the main menu, such as when the CNA is reviewing or documenting information. Through a command, such as "Review reminders" (see FIG. 8), the CNA can access the information that the reminder earcon refers to.

An incoming page earcon is generally triggered when there is a page that is available for the CNA. For example, if another CNA or nurse pages the particular CNA and leaves a recorded message, a page earcon may be triggered. Again, the page earcon may include the incoming page tone 170, followed by a speech dialog associated therewith, and then followed by another incoming page tone 170 in response to a page status change while the user is at the main menu, in response to a user navigating to the main menu while there is a page outstanding, and/or in response to a predetermined time period elapsing while a voice assistant 45 is in the sleep mode and there is a page outstanding. Alternatively, the page earcon may include only the incoming page tone 170 in response to a page status change when the CNA is not at the main menu, such as when the CNA is reviewing or documenting information. Through a command, such as "Review pages" (see FIG. 8), the CNA can access the information that the page earcon refers to.

In some embodiments, if a care plan has been updated, a page earcon occurs such that the CNA can be alerted to updates. In those embodiments, the page earcon includes speech dialog that indicates "You have an update." In that way, updates can be handled in a timely fashion, and the CNA can issue the command "Review updates" in response to the page earcon.

In some embodiments, earcons may be provided to the CNA when the CNA returns to the main menu and there is an outstanding page and/or reminder. Until the CNA has addressed the information or tasks associated with a particular page or reminder, the respective earcon associated therewith will be provided each time that CNA returns to the main menu. However, if a page or reminder status changes multiple times while that CNA is not at the main menu, such as when the CNA is reviewing or documenting information, the respective single tone earcon is provided once. For example, if a CNA receives two pages while that CNA is reviewing or documenting information, the respective page earcon (which includes only the incoming page tone 170, as the CNA is not at the main menu) is provided when the first page is received but not when the second page is received. Moreover, the timing of when an earcon is provided is determined intelligently. For example, if the voice assistant 45 is waiting for speech input from the CNA, an earcon may be delayed until such time as that speech input has been received but before another wait for additional speech input and/or speech dialog. In some embodiments, providing earcons while the CNA is not at the main menu is a configurable option. As such, earcons, and particularly earcons that include a tone, associated speech dialog, and the tone a second time, may not be provided outside of the main menu and/or the sleep mode.

In regard to the sleep mode, an earcon may be played after a predetermined time while a voice assistant 45 is in the sleep mode when there is a page and/or reminder outstanding. For example, when there is a page and/or reminder outstanding and when the voice assistant is in the sleep mode 45, a corresponding earcon may be provided about every 80 seconds. It will be appreciated by one having ordinary skill in the art that the corresponding earcon (e.g., for a page and/or reminder) may be played more or fewer than about every 80 seconds while the voice assistant is in sleep mode.

Those of ordinary skill in the art will appreciate that other tones, speech dialogs and/or earcons (including sequences of tones and or speech dialogs in earcons) may also be supported, and that many variations are consistent with the embodiments of the invention. For example, CNAs may be able to set their preferences regarding the tones/speech dialogs/earcons that are provided, when those tones/speech dialogs/earcons are provided, whether or not to remind about a task, etc. Moreover, a CNA may prefer to not be interrupted while performing a task, and as such, if the CNA is interacting with the system but away from the main menu, any tones, speech dialogs and or earcons to be provided may be postponed until after the CNA completes the interaction in an effort to avoid interrupting the CNA and to avoid the perception of vocally directing the CNA. Indeed, consistent with the principles of the present invention, the voice assistant 45 seeks to minimize the interruptions to the CNA, and instead, the tones, speech dialogs and/or earcons may simply indicate that there is a reminder or a page for the CNA to listen to and make the reminders and pages available for the CNA to listen to via the main menu 63 when the CNA desires. As such, if the CNA is busy or otherwise unable to listen to a reminder, for example, because they are with a resident, the CNA may listen to the reminder later on as desired and constant interruptions may be reduced.

Therefore, embodiments of the invention provide near realtime voice messaging as a communication mechanism without undesired interruption. The voice user interface provides information about the workflow of the CNA and the appropriate times for the CNA to be interrupted. The voice user interface provided by embodiments of the invention slots the notification into the workflow when appropriate using audible earcons, which may include audible tones, speech dialogs or combinations thereof Thus, information about the status of communications is conveyed without disruption of a workflow.

Figure 7:
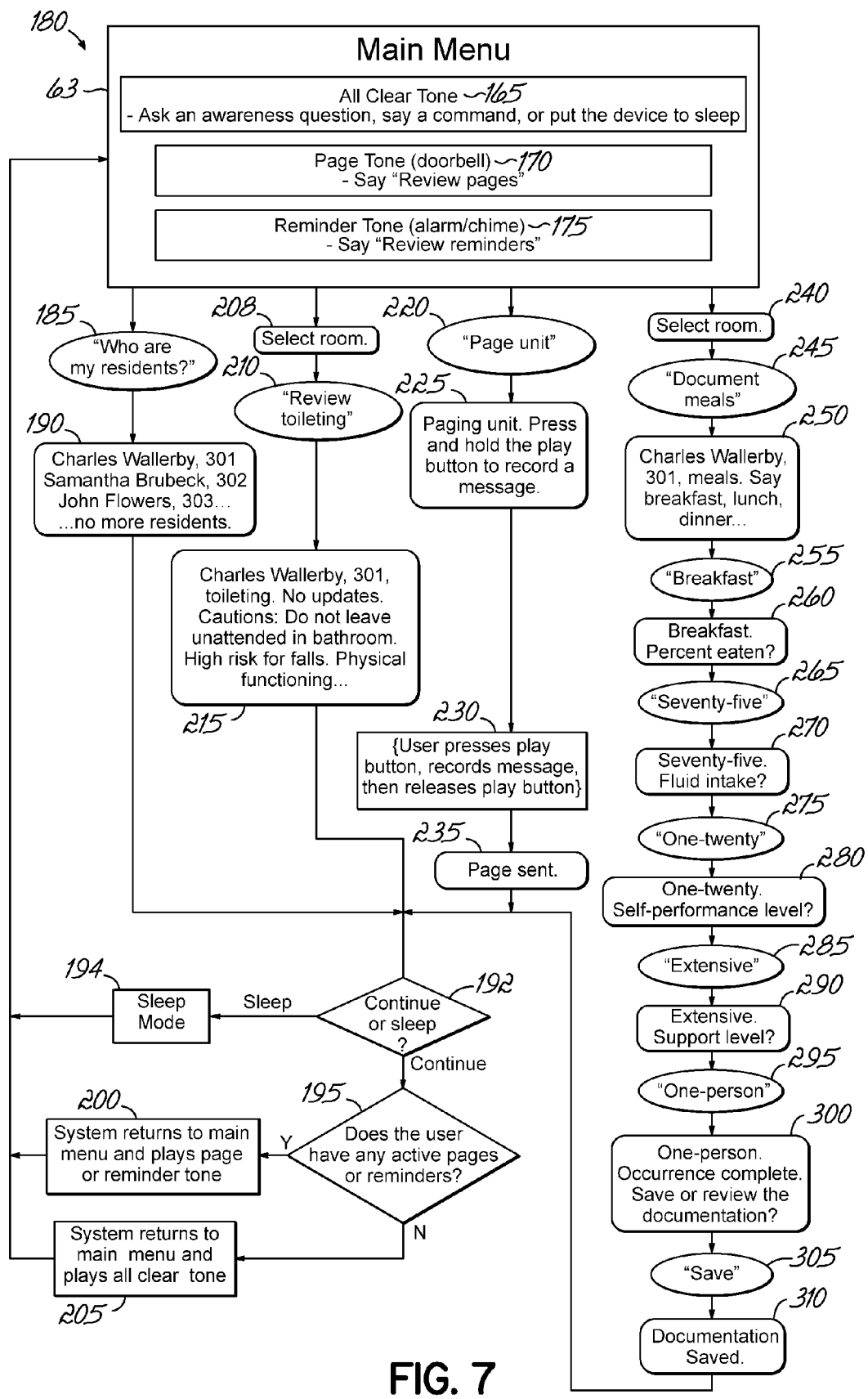
FIG. 7 is an exemplary main menu routine executed by the voice assistant system of FIG. 1 consistent with the principles of the present invention.

Tuning now to FIG. 7, that figure illustrates an exemplary voice dialog and workflow routine 180 executed by the voice assistant system 5 depicting interaction between the CNA and the main menu 63. First, the CNA logs on ad the care plans of the assigned residents and the facility configuration data, as well as any other pertinent data, may be sent to the voice assistant of the CNA as explained hereinabove. After logging on, the CNA may hear the all clear earcon indicating that there a-e no active pages or reminders, and the CNA may "sit" in the main menu 63 of the voice dialog until the CNA desires to ask a Situational Awareness Question, say a command, or put the voice assistant 45 to sleep. While the CNA sits in the main menu 63, the voice assistant 45 may be awake and using its speech recognition capabilities to actively listen for speech input, interpret the speech input and/or determine if the CNA has spoken a valid parameter that is used in the voice dialog of the invention. The CNA may put the voice assistant 45 to sleep when the CNA wants to speak (e.g., to a resident) but does not want the voice assistant 45 to use its speech recognition capabilities and other functionalities. In some embodiments, the voice assistant 45 enters a sleep mode after a predetermined time during which is idle (e.g., including at the main menu 63), such as, for example, about 20 seconds.

When the CNA decides to ask a Situational Awareness Question, the CNA may say that Situational Awareness Question in block 185. For illustration; the voice or speech input of the CNA is illustrated in blocks in the form of ovals, the speech dialog (e.g., generated speech) from the voice assistant 45 is illustrated in blocks in the form of rounded rectangles. Returning back to block 185, the CNA may ask, "Who are my residents?" In response to the Situational Awareness Question, the CNA may be provided with the speech dialog in block 190, indicating the name and room number of each assigned resident, such as, "Charles Wallerby, 301; Samantha Brubeck, 302; John Flowers, 303 . . . no more residents."

Next, control may pass to block 192 to determine if the CNA desires to continue to the main menu 63 or put the voice assistant 45 to sleep. Specifically, the voice assistant 45 may provide a speech dialog that asks "Continue or sleep?" When the CNA chooses to put the voice assistant 45 to sleep ("Sleep" branch of decision block 192), the CNA may use the "Sleep" command (FIG. 8) to enter a sleep mode as shown at block 194. In the sleep mode, the voice assistant 45 may continue to determine whether there is at least one page and/or reminder outstanding, but otherwise wait to detect a button press of a button of the voice assistant 45 to continue converting speech input into machine readable input. In the sleep mode, the voice assistant 45 may provide an earcon corresponding to a page and/or reminder in response to receiving a page and/or reminder. That earcon may be repeated every 80 seconds. Upon exiting sleep mode (block 194), the voice assistant may proceed to the main menu 63.

When the CNA wants to continue by using a "Continue" command ("Continue" branch of decision block 192), control may pass to block 195 to determine if the CNA has any active pages and/or reminders. If there is at least one active page and/or reminder ("Yes" branch of decision block 195), control may then pass to block 200, and the voice assistant 45 may return to the main menu 63 as well as provide the page earcon and/or the reminder earcon when there is at least one outstanding page and/or reminder, respectively. When there is not at least one outstanding page and/or reminder ("No" branch of decision block 195), control may pass to block 205, and the voice assistant 45 may return to the main menu 63 as well as provide the all clear earcon. Upon returning to the main menu 63, the CNA may issue a command to the voice assistant, and may say "Review pages" if the CNA hears the page earcon or say "Review reminders" if the CNA hears the reminder earcon. The voice assistant 45 may then play the respective dialog regarding a page or reminder, respectively. After the pages or reminders have been reviewed, the all clear earcon may be provided.

To continue the example, the CNA may decide to perform tasks associated with one of the residents (in the context of this example, which is not intended to limit embodiments of the invention, Charles Wallerby). As such, the CNA may choose from a variety of voice user interface parameters in the form of commands. In particular, the CNA may select a resident, and may say, "Select Room 301" (block 208), which is Charles Wallerby's room number. The CNA may then request information regarding the care for that resident. For example, "Review toileting" (block 210) might be spoken. When the CNA reviews certain information from the care plan, it may be read to the CNA, including the checked fields in the care plan (e.g., FIGS. 2A, 2B). For example, the CNA may be provided with speech dialog in block 215 based on the care plan of a resident and/or other information on the voice assistant 45. For example, this speech dialog may be "Charles Wallerby, 301, toileting. No updates. Cautions: Do not leave unattended in bathroom. High risk for falls. Physical functioning . . . " (block 215). As such, the speech dialog provides information about the resident's care plan and assists the CNA by warning the CNA that Charles Wallerby should not be left unattended in the bathroom and is at a high risk for falls. Next, control may pass to the blocks 192, 194, 195, 200 or 205 as appropriate, and then to the main menu 63 as described hereinabove. As will be understood, various other care plans may be reviewed in a similar fashion. The voice assistant 45 thus interacts with the various care plans as necessary as directed by the CNA. As will be appreciated, the speech dialog resulting from the various commands and/or Situational Awareness Questions will vary based upon the fields selected in a care plan and other information about the resident contained in the system.

An overview of what tasks remain within a shift may be obtained by the CNA by utilizing a Situational Awareness Question of, "Who needs care?" 125. The CNA is provided with a list of the residents who still need various care procedures, or for whom certain tasks are still outstanding. Then, knowing such information, the CNA can then select a particular resident for their attention. For example, a resident could be selected, and then the command "Review care" 145 will indicate to the CNA what tasks or care procedures still remain for that particular resident.

Alternatively, the CNA may say, "Page unit" (block 220), and may be provided with the speech dialog in block 225 stating, "Paging unit. Press and hold the play button to record a message." Next, the CNA may press a play button on the voice assistant 45 to begin recording, record the message, and then release the play button as indicated in block 230, and the page may be sent to all of the employees in the unit in block 235 wearing voice assistants 45. Control may then pass to blocks 192, 194, 195, 200 or 205 as appropriate, and then to the main menu 63 as described hereinabove. It will be appreciated that, in some embodiments, pages may be sent to less than all employees in a unit wearing a voice assistant 45. As such, pages may be selectively addressed to one, or a subset of (e.g., one, some or all), all those wearing a voice assistant.

To complete tasks for a resident and document those tasks, the CNA may say "Select Room 301" (block 240), which is Charles Wallerby's room number, and then "Document meals" (block 245). As such, the CNA may be provided with speech dialog that corresponds to the "Document meals" command, such as that illustrated ill blocks 250, 260, 270, 280, 290, 300, and 310. Specifically, block 250 acknowledges the intentions of the CNA to document meals and indicates the predetermined vocabulary that the CNA may say when documenting a meal by stating "Charles Wallerby, 301, meals, Say breakfast, lunch, dinner . . . " After the CNA says "breakfast" (block 255), block 260 acknowledges the documentation of breakfast and requests the CNA to indicate the percentage eaten by Charles Wallerby by stating "Breakfast. Percent eaten?" The CNA may respond with "Seventy-five" (block 265) and may then hear "Seventy five. Fluid intake?" (block 270). The CNA may respond to this request with "One-twenty" (block 275) and may then hear "One-twenty. Self-performance level?" (Block 280). The CNA may respond with "Extensive" (block 285) and may then hear "Extensive. Support Level?" (Block 290). The CNA may respond with "One-person" (block 295) and may then hear "One-person. Occurrence complete. Save or review the documentation?" (Block 300). In that way, various data associated with a particular task is handled and documented by the voice assistant. It will be appreciated that alternative values other than those illustrated and described herein may be documented without departing from the scope of embodiments of the invention.

As may be appreciated, other data associated with other care plan segments may be captured in similar fashion with other appropriate voice dialogs that are reflective of the particular care plan and the fields therein. For example, "Document hygiene" may have a voice dialog associated with that portion of the care plan.

The self-performance and the support levels generally refer to the amount of assistance that the resident needed, and may vary based upon the activity. The different self-performance levels and support levels that the CNA may say are illustrated in document 62 in FIG. 4, along with the Situational Awareness Questions and commands that the CNA may say. Next, the CNA may say "Save" (block 305) and may then hear "Documentation saved." (block 310). Control may then pass to the blocks 192, 194, 195, 200 or 205 as appropriate, and then to the main menu 63 as described hereinabove.

Figure 8:
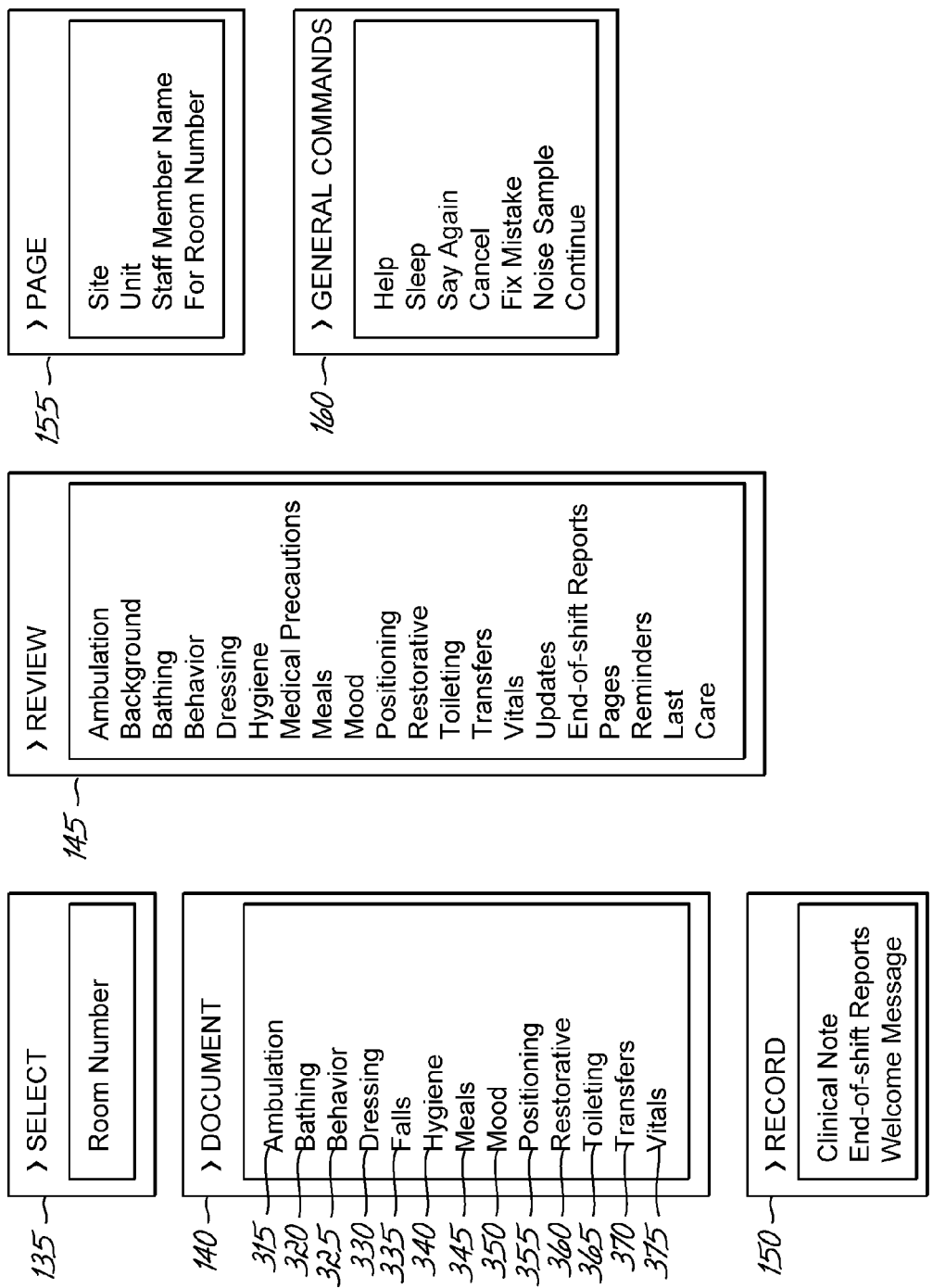
FIG. 8 is a detailed view of the parameters in the form of commands from the main menu of FIG. 5 consistent with the principles of the present invention.
Figure 9:
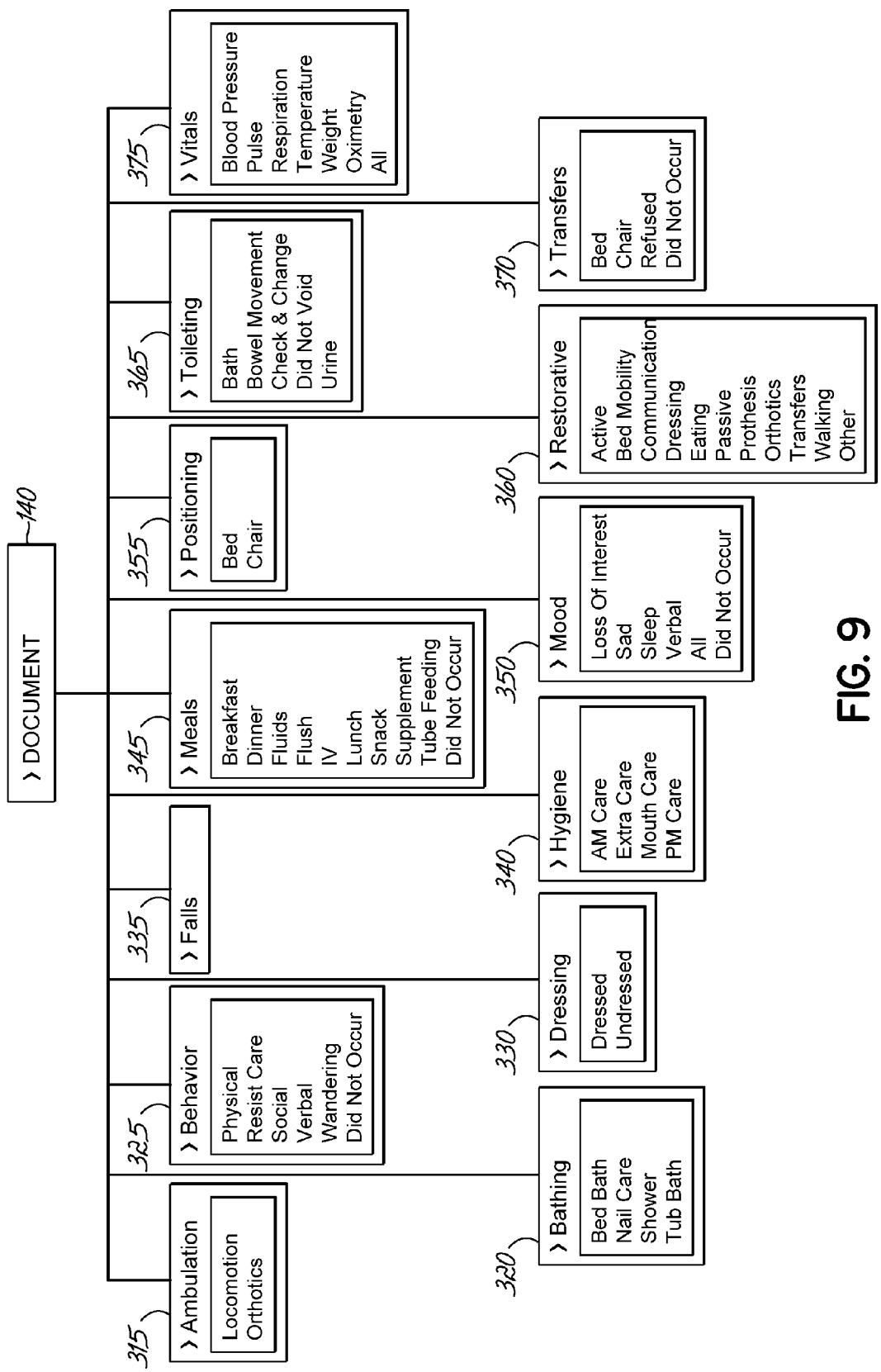
FIG. 9 is a detailed view of the document command from FIG. 8 consistent with the principles of the present invention.

Turning now to FIGS. 8-9, these figures illustrate in more detail some of the commands, sub-commands, and information that the CNA may choose via the main menu 63. One of ordinary skill in the art will appreciate that the commands and sub-commands are utilized to facilitate discussion related to the embodiments of the invention and are consistent with the principles of the present disclosure but not otherwise intended to be limiting. Similarly, one having ordinary skill in the art will appreciate that the information that may be chosen by the CNA in response to the speech dialog provided is also not intended to be limiting. FIGS. 8-9 are merely illustrative of details of various items, with the hierarchy from broadest to narrow being command, sub-command, and information. Furthermore, those of ordinary skill in the art will appreciate that each command and sub-command combination may be associated with a separate executable routine and may provide different speech dialog as necessary to facilitate the task. For instance, many command and sub-command combinations were already illustrated in connection with the blocks 210, 220, and 245 in the routine 180 in FIG. 7, and although illustrated as a single routine 180, each one of these may be a separate routine with at least one speech dialog.

Turning to FIG. 8, the "Select" command 135 may be utilized to select a room number, and then the "Document" command 140 or the "Review" command 145 may be chosen by the CNA. Starting with the "Document" command 140, a variety of tasks indicated by the various resident care plans may be performed by the CNA and documented via the "Document" command 140 and the sub-commands that correspond with that task. Some of the sub-commands are illustrated under the "Document" command 140. The sub-commands may be, but are not limited to, "ambulation" 315, "bathing" 320, "behavior" 325, "dressing" 330, "falls" 335, "hygiene" 340, "meals" 345, "mood" 350, "positioning" 355, "restorative" 360, "toileting" 365, "transfers" 370, and/or "vitals" 375. Various of the sub-commands correspond to the care plans, as discussed herein with respect to FIGS. 2A-2B and 12-22. And each one of these subs commands may have information for the CNA to choose, as illustrated in FIG. 9. For example, the CNA may choose the "Document" command 140 and the "ambulation" sub-command such that the CNA is prompted by speech dialog associated with the combined "Document ambulation" commands to choose between locomotion or orthotics for documentation purposes (FIG. 9). Next, the CNA may be provided with the appropriate speech dialog based upon whether locomotion or orthotics was chosen. Such a speech dialog may, for example, consist of a series of questions for the CNA to answer as set forth in the example of FIG. 7.

In another example, the CNA may choose the "all" term as illustrated in FIG. 9 to document all of the information for a certain sub-command, like "vitals" 375 or "mood" 250. Also, in some instances, the CNA may have to choose the "did not occur" terminology to affirmatively document that a task did not occur (e.g., "meals" 345 or "transfers" 270), or the "did not void" terminology for "toileting" 365 to indicate that the resident did not have to go to the bathroom (see FIG. 9).

Returning to FIG. S, each of the sub-commands (and tasks) listed under "Document" command 140 may also be utilized with the "Review" command 145 such that the CNA may review any of these portions of the care plan during his or her shift. The CNA may additionally review "medical precautions," "updates" (e.g., to a care plan), "end-of-shift reports" (e.g., recorded by the nurses indicating information that the CNA should be aware of), "pages," "reminders," "last" (e.g., last weight, last urine, last bowel movement, last meals, last vitals, last fluids, etc.) and/or "care" (e.g., to see what tasks are outstanding for a resident).

Next, the CNA may also use the "Record" command 15D and the "clinical note" sub-command to record a clinical note. In particular, the clinical note may be recorded to inform a nurse of a problem or indicate some other observation of the CNA. Upon recording the clinical note, the clinical note may be transmitted from the voice assistant 45 of the CNA to the nursing workstation 20 for the nurse to address. Additionally, the nurse may be provided with a page earcon on their own voice assistant 45 to indicate that a clinical note has been received. As such, this process may ensure that the nurses address each clinical note recorded and that the corresponding care plan is updated as needed at the workstation 20 by the nurse.

Furthermore, with respect to the "Record" command 150, the sub-command of the "end-of-shift reports" and "welcome message" may be reserved for the nurses. In particular, a nurse may utilize the "end-of-shift reports" sub-command to record the reports during or after a meeting with the CNAs at the end of the shift, for example, in order to inform the CNAs scheduled for the next shift of anything that they should be aware about. The "welcome message" sub-command may be utilized to record a message that is sent to everyone with a voice assistant 45. An audible earcon, such as a page earcon, may alert a CNA to such a welcome message.

Although the CNAs may be restricted in their ability to utilize these sub-commands, a CNA may utilize the "Page" command 155 and the sub-commands associated therewith to page the site, to page a unit, to page a particular staff member by using the staff member's name and/or to page for a room number. Furthermore, the CNA may choose the "General" command 160 and sub-commands listed below it to request help with acceptable terminology that the CNA may say, place the voice assistant 45 to sleep and /o have the voice assistant 45 repeat the last speech dialog or say again. Moreover the CNA may utilize the sub-commands listed under the General Commands 160 to cancel, fix a mistake and/or to perform a sample of the background noise of the current environment.

Figure 10A:
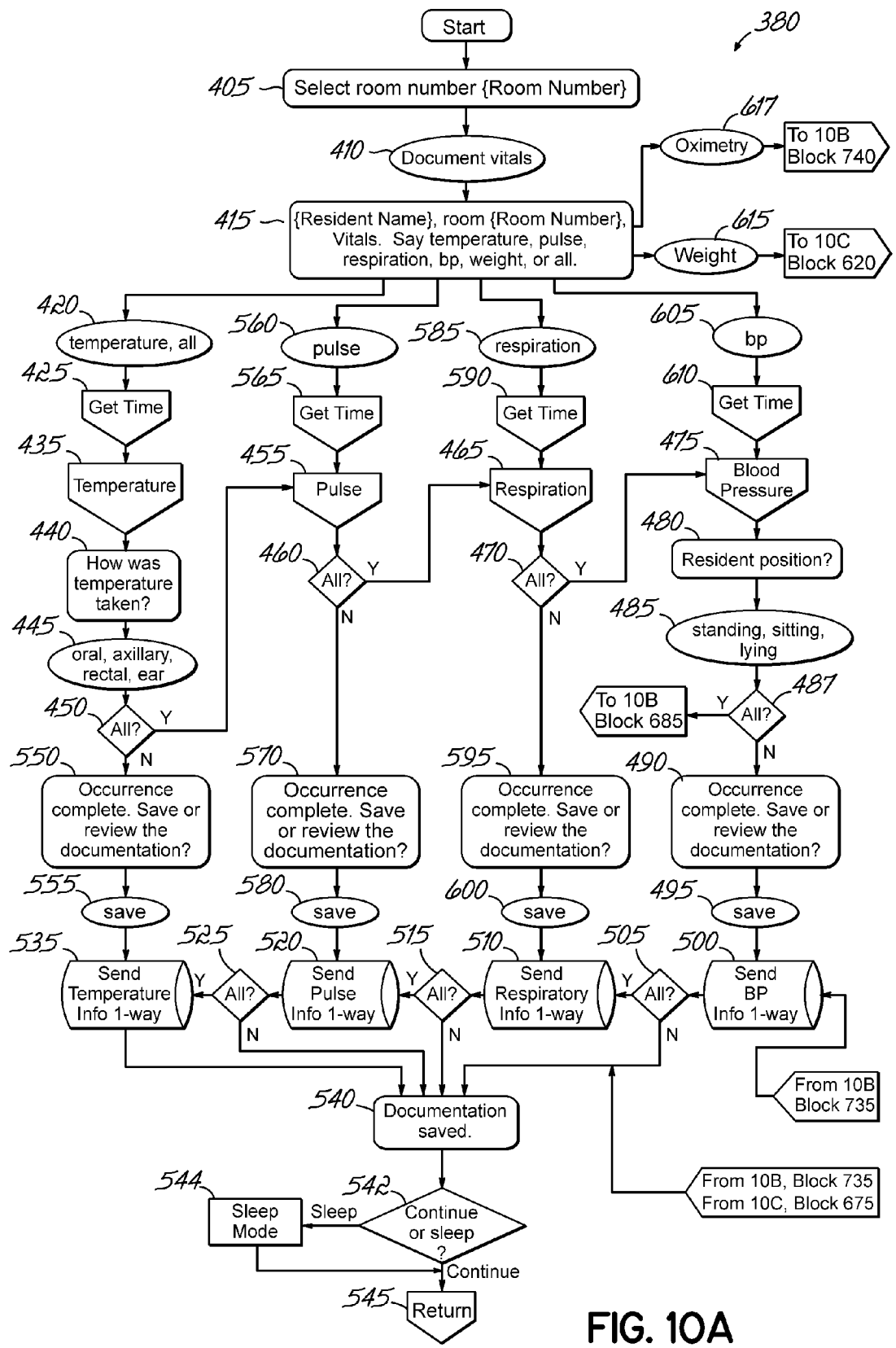
FIGS. 10A-10B is an exemplary documentation of a vitals routine executed by the voice assistant system of FIG. 1 consistent with the principles of the present invention.

FIGS. 10A-10C and FIG. 11 illustrate an exemplary documentation routine. As discussed in connection with FIG. 9, various vitals might be documented along with other information. Referring to FIG. 10A, the exemplary routines may include a documentation of vitals routine 380, a weight analysis routine 390 (which may be, in turn, included in the documentation of vitals routine 380)) and a weight routine 400 (which may be, in turn included in the weight analysis routine 390), respectively. The routine 380 assumes that the CNA chose the "Document" command 140, the sub-command "vitals" 355, and the additional sub-command "all". As such, the exemplary routine 380 may be executed and may call routines 390 and 400 during its execution. As before, the CNA's speech input is illustrated in ovals while speech dialog from the voice assistant 45 is illustrated in rounded rectangles.

Figure 10B:
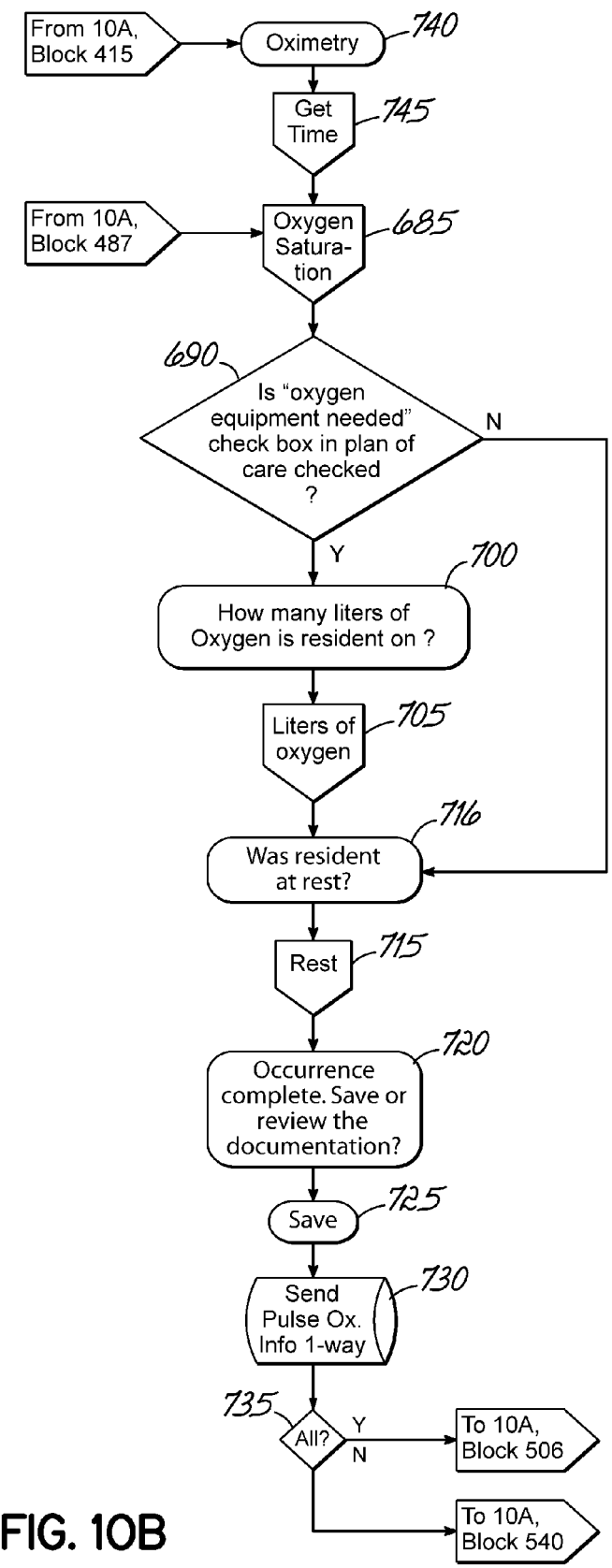
Figure 10C:
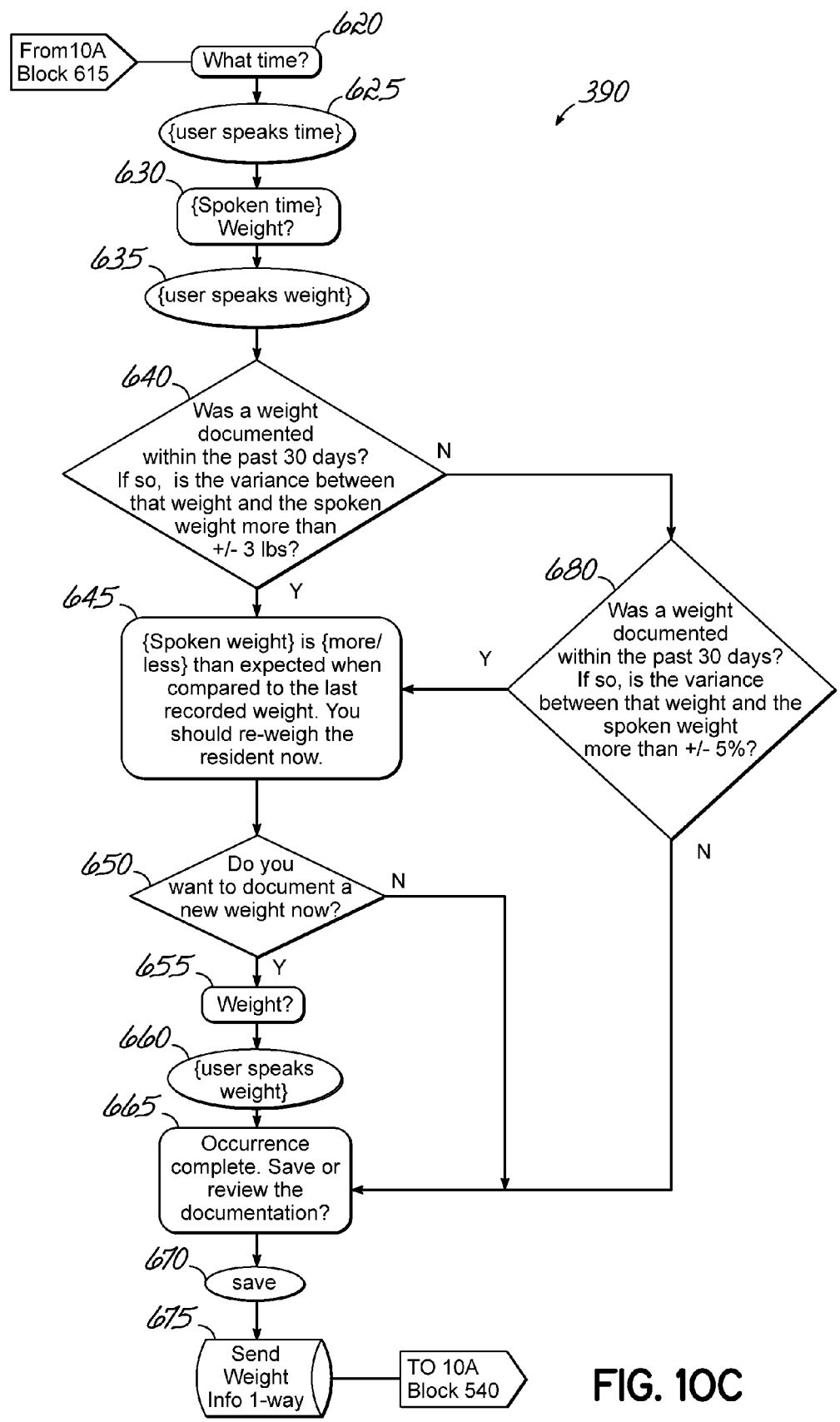
FIG. 10C is an exemplary weight analysis routine that may be called from the documentation routine of FIGS. 10A-10B and that is also executed by the voice assistant system of FIG. 1 consistent with the principles of the present invention.

Turning to FIGS. 10A-10C and routine 380, when the CNA decides to engage in tasks related to the vitals of a resident, the CNA may say "Select room {Room Number}" (block 405), with the "Room Number" insert being the room number of the resident. The CNA may then say "Document vitals" (block 410). Upon receiving these commands, the voice assistant 45 may say "{Resident Name}, room {Room Number}, Vitals. Say temperature, pulse, respiration, BP, oximetry, weight, or all," (Block 415). The CNA may choose any of the vitals individually and the appropriate path may be followed in the speech dialog via routine 380, but in this example, the CNA chooses to document "all" vitals (block 420). As such, control may pass to block 425 to get the time.

In some embodiments, block 425 may call a "get time" routine to determine and verify the current time. Specifically, the "get time" routine may determine a time then provide that time to the CNA through a speech dialog to verify. Alternatively, the CNA may be provided with speech dialog requesting they speak the time. Next, control may pass to block 435 to call a temperature routine to determine the temperature of the resident. Block 440 may asks the CNA to state "How was the temperature taken?", and the CNA may say "oral," "axillary," "rectal," or "ear" (block 445).

When the CNA indicates that all the vitals are to be documented ("Yes" branch of decision block 450), control may then pass to block 455 to call a pulse routine to document a pulse of the resident and then to block 460 and block 465 for other vitals. The block 465 may call a respiration routine to document a respiration of the resident, and then to block 470 and block 475, with block 475 calling a blood pressure, or "bp," routine to document a bp of the resident. Next, the CNA may be asked to provide the position of the resident when the blood pressure was taken at block 480. The CNA may say standing, sitting, or lying (block 485), and then control may pass to block 487 and block 685, with block 685 calling for an oxygen saturation, or "oximetry," routine to document a pulse-oxygen level of the resident. Next, the system may check to see if an "oxygen equipment needed" check box in a care plan is checked (block 690). When the check box is checked ("Yes" branch of decision block 690) the CNA may be asked how many liters of oxygen the resident is on (block 700). The CNA may then indicate the number of liters of oxygen the resident is on (block 705). After documenting the number of liters of oxygen the resident is on (block 705) or if the system determines that the check box for indicating whether oxygen equipment needed is not checked ("No" branch of decision block 690), the CNA may be asked whether the resident was at rest (block 710). The CNA may then indicate whether the resident was at rest or not (block 715), and then control may pass to block 720 to state "Occurrence complete. Save or review documentation?" when the CNA states "save" (block 725) control may pass to block 730 to send the pulse oximetry information one way (e.g., to the voice transaction manager 35). Likewise, control may pass to blocks 735, 500, 505, 510, 515, 520, 525, and 535 to send the blood pressure information, respiration information, the pulse information, and the temperature information one way for storage. Next, control may pass to block 540, which states "Documentation saved", and then to block 542 to determine whether to continue or sleep. When the CNA indicates to put the voice assistant to sleep ("Sleep" branch of decision block 542) the voice assistant may enter a sleep mode (block 544). When the CNA chooses to continue ("Continue" branch of decision block 542) and/or after the sleep mode (block 544), the voice assistant may return to the main menu (block 545).

However, if the CNA chooses to individually document the temperature, for example, control may pass through items 450, 550, 555, 535, 540, 542, 544 and/or 545, as previously described. If the CNA only wants to document the pulse, control may flow from block 415 through the path that includes items 560, 565, 455, 460, 570, 580, 520, 525, 540, 542, 544 and/or 545. If the CNA only wants to document the respiration, control may flow from block 415 through the path that includes items 585, 590, 465, 470, 595, 600, 510, 515, 540, 544 and/or 545. Moreover, if the CNA only wants to document the blood pressure, control may flow from block 415 to items 605, 610, 475, 480, 485, 490, 495, 500, 505) 540, 544 and or. Similarly, if the CNA only wants to document oximetry, control may flow from block 415 to items 617, 740, 745, 685, 690, 700, 705, 710, 715, 720, 725, 730, 735, 540, 544 and/or 545.

It is worth noting that in the illustrated routine 380, weight was not one of the vitals that was documented when the CNA indicated that they wanted to document "all," but those of ordinary skill in the art will appreciate that in other embodiments, weight may be included when the CNA chooses to document all. As such, attention will now turn to documentation of the weight. Starting with block 415, if the CNA only wants to document the weight of the resident (block 615), control may pass to the weight analysis routine 390 and the appropriate speech dialog as illustrated in FIG. 10C.

Figure 11:
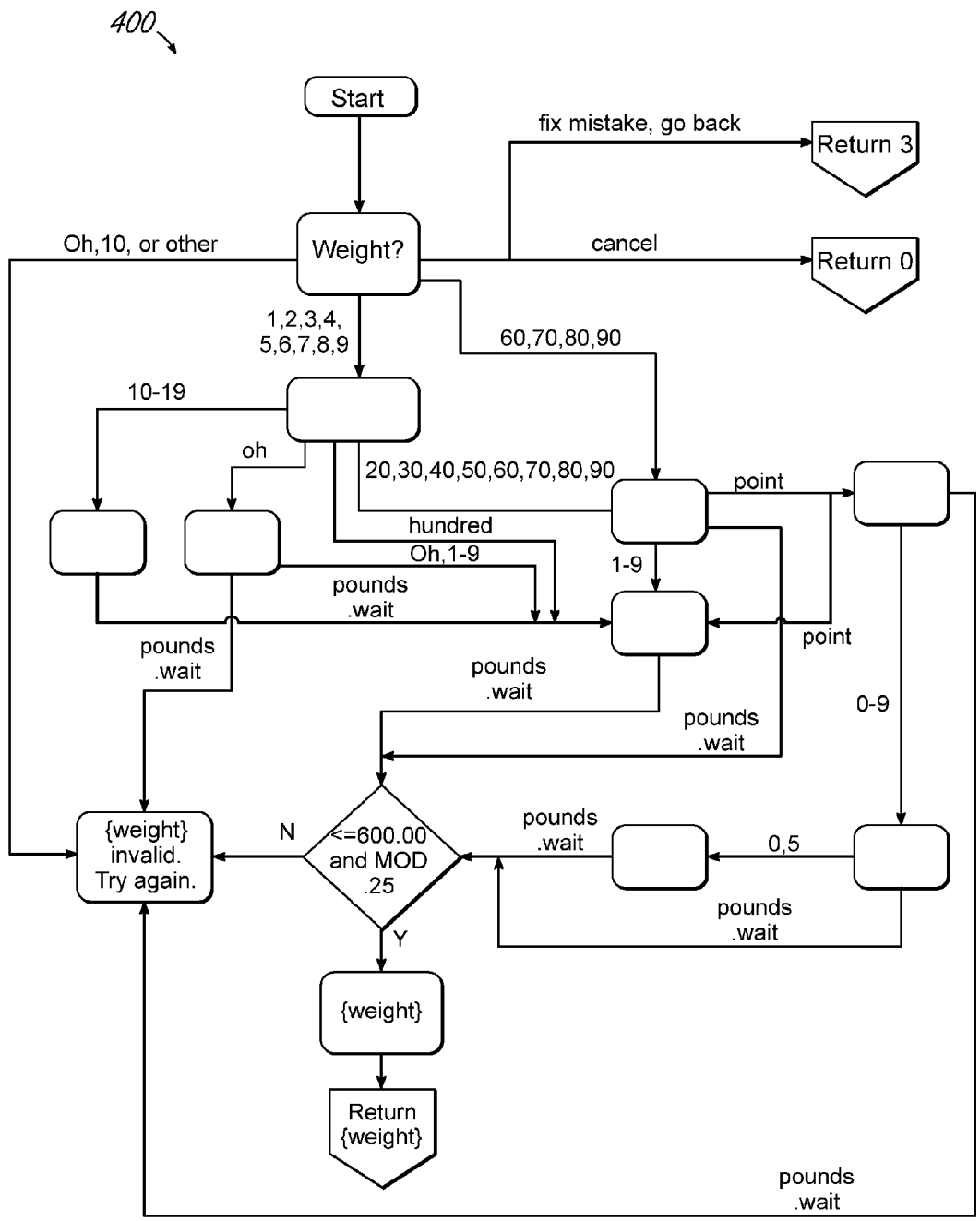
FIG. 11 is an exemplary weight routine that may be called from the weight analysis routine of FIG. 10C, and that is also executed by the voice assistant system of FIG. 1 consistent with the principles of the present invention.

As illustrated in FIG. 10C and the weight analysis routine 390, block 620 may ask the CNA for the time, and the CNA may speak the time at block 625. Next, block 630 may repeat the spoken time and ask the CNA for the weight; and the CNA may speak the weight as noted at block 635 (which may be obtained from a scale used to weigh the resident). In the corresponding exemplary weight speech recognition routine 400 as shown in FIG. 11, the weight is captured. In routine 400, the CNA's speech is illustrated on the lines, and as the CNA speaks the numbers, different paths are traversed. In particular, routine 400 illustrates a corrective routine that intelligently determines the weight of the resident based on the speech input from the CNA. For example, the weight is also checked to determine it is a valid weight, and if it is, the weight is returned to routine 390. As may be appreciated, other weight speech recognition routines might be used to capture the spoken weight.

Nonetheless, with reference once again to the routine 390, regardless of how the weight is determined, control may pass to block 640. Block 640 determines if another weight has been documented for that same resident in the past three days. If so, block 640 determines if a variance (e.g., difference, differential) between that previous weight and the spoken weight from block 635 is more than about three pounds lower or more than about three pounds higher. However, those of ordinary skill in the art will appreciate that the variance may be compared to other preselected values consistent with the principles of the present invention, and may be based on, for example, best practices.

If the variance is about three pounds lower or about three pounds higher, control may pass to block 645 to indicate to the CNA that the spoken weight is more or less than expected when compared to the last recorded weight. Moreover, the block 645 also indicates to the CNA that he or she should re-weigh the resident now. Next, control may pass to block 650 to determine if the CNA wants to document another weight, and if so, control may pass to items 655 and 660 to receive another weight, such as per routine 400. The CNA may then be provided with an indication that the occurrence is complete, and asked whether to save or review the documentation at block 665. After the CNA says "save" (block 670), control may pass to block 675 to send the weight information one way (e.g., to the voice transaction manager 35), and then back to routine 380 in FIGS. 10A-10B for the nurse assistant to inform the CNA that the documentation has been saved (block 540), to determine whether to continue or sleep (block 542), to enter a sleep mode (block 544) and or to proceed to the main menu (block 545).

Returning to block 640 in routine 390 in FIG. 10C, if a weight was not documented within the last three days, control may pass to block 680 to determine if a weight was documented within the past 30 days. If so, block 680 determines if a variance between the current weight and the weight of the past 30 days has more or less than about a five percent differential. If the differential is about five percent, control may pass to block 645 for the voice assistant to suggest to the CNA that the resident should be re-weighed, as previously discussed. Otherwise, control may pass to block 665, as previously discussed.

Those of ordinary skill in the art may appreciate that by immediately analyzing the weight for the CNA, by comparing the weight the CNA is entering to the previously entered weight at the point of care (e.g., at the scale), the CNA may be able to avoid documenting an erroneous weight, and may immediately weigh the resident again and provide a new weight. This presents a significant time savings in resident care, because normally an improper weight would not be noticed until significantly later and would require a duplicated, time consuming, and possibly difficult and intrusive effort to get the resident re-weighed. The present invention provides verification right at the point of care. Alternatively, if the weight is correct but lower than it should be, for example, the CNA may immediately learn about the lower weight and inform a nurse (e.g., by recording a clinical note an or page). In turn, the nurse may adjust a care plan of the resident, including adding warnings that the resident may be at a high risk for fails due to the lower weight, as needed. Indeed, those of ordinary skill in the art will appreciate that with the immediate weight analysis provided by the invention, the CNA may be assisted with weighing a resident and may learn about an anomalous weight thereof at the point of care to avoid having to transport the resident to the scale again for re-weighing days or weeks later. Rather, the appropriate actions may be taken immediately for a correct but possibly anomalous weight.

While the present invention has been illustrated by the description of the embodiments thereof, and while the embodiments have been described in considerable detail, it is not the intention of the application to restrict or in any way limit the scope of the appended claims to such detail. Additional advantages and modifications will readily appear to those skilled in the art. Therefore, the invention in its broader aspects is not limited to the specific details or representative apparatus and method, and illustrative examples shown and described. For example, the principles of the present invention may be adapted for a setting different than a nursing home. Accordingly, departures may be made from such details without departure from the spirit or scope of applicant's general inventive concept.

What is claimed is:

1. A method of assisting a user in providing care to residents of a care facility, the method comprising:

storing at least one care plan in a voice assistant device carried by a user, the care plan defining a plurality of tasks to be performed by the user as part of a workflow in providing care to the residents;

capturing speech input from the user with the voice assistant device and providing speech processing, including speech recognition and speech synthesis, at the voice assistant device;

determining, from the processed speech input, a selected interaction with a care plan, and in response to the selected interaction, providing a speech dialog with the user through the voice assistant device that is reflective of the care plan;

including in the speech input a speech command for selecting a type of interaction with the care plan and at least one subsequent speech sub-command reflective of tasks that are performed by the user or of care provided according to a pertinent part of the care plan;

utilizing a plurality of earcons at selected times in the course of the speech dialog, the earcons having individual audible tones for indicating the existence of at least one of an active page or reminder for the user or the lack of said active page or reminder.

2. The method of claim 1, wherein the care plan is associated with care provision for a resident of at least one of a care facility or medical facility.

3. The method of claim 2, wherein a selected interaction with the care plan provides assistance to the user in documenting at least one of the care or treatment of the resident.

4. The method of claim 1, wherein the speech dialog assists with identifying information to be input through speech input of the user.

5. The method of claim 1, wherein the speech dialog includes an interrogatory for identifying information to be input through speech input of the user.

6. The method of claim 1, wherein the speech input includes requesting any care plans associated with the user for performance by the user.

7. The method of claim 1, wherein the speech input includes an interrogatory selected from the group of interrogatories consisting of: an interrogatory regarding at least one resident cared for by the user, an interrogatory regarding at least one resident that needs their vital signs documented, an interrogatory regarding at least one resident that is associated with an update, an interrogatory regarding at least one resident that needs restorative care, an interrogatory regarding at least one resident that needs care, an interrogatory regarding at least one resident that needs bathing, an interrogatory regarding the most important tasks currently assigned to the user, an interrogatory regarding recent changes to at least one of tasks or at least one resident currently assigned to the user, an interrogatory regarding tasks that are yet to be completed that are in turn associated with the user, an interrogatory regarding tasks that are scheduled that are in turn associated with the user, an interrogatory regarding the identity of another user assigned to at least one resident, or an interrogatory regarding the contents of a shift report from a previous shift.

8. The method of claim 1, wherein the speech input includes an interrogatory that includes at least one situational awareness question to make a user aware of the tasks of their workflow for at least one resident, the method further comprising answering the situational awareness question with a speech dialog.

9. The method of claim 1, further comprising:
in response to the voice assistant device determining that there is an outstanding page associated with the user, providing a page earcon with a unique tone to the user indicating the outstanding page for the user.

10. The method of claim 9, wherein the page earcon includes a speech dialog indicating the number of outstanding pages for the user.

11. The method of claim 9, further comprising:
determining, from an additional speech input of the user captured with the voice assistant device, an interaction to play the outstanding page; and
in response to determining the interaction to play the outstanding page, playing the outstanding page audibly for the user.

12. The method of claim 1, further comprising:
in response to the voice assistant device determining that there is an outstanding reminder associated with the user, providing a reminder earcon with a unique tone to the user indicating the outstanding reminder for the user.

13. The method of claim 12, wherein the reminder earcon includes a speech dialog indicating the number of outstanding reminders for the user.

14. The method of claim 12, further comprising:
determining, from an additional speech input of the user captured by the voice assistant device, an interaction to play the outstanding reminder; and
in response to determining the interaction to play the outstanding reminder, playing the outstanding reminder.

15. The method of claim 1, further comprising:
in response to the voice assistant device determining that there are no outstanding reminders or pages associated with the user, providing an all clear earcon with a unique tone to the user indicating that there are no outstanding reminders or pages associated with the user.

16. The method of claim 15, wherein the all clear earcon includes a speech dialog indicating that there are no outstanding reminders or pages associated with the user.

17. The method of claim 1, further comprising:
dynamically receiving, with the voice assistant device, at least one update to a care plan; and
in response to receiving the at least one update, providing a page earcon to the user indicating receipt of the at least one update.

18. The method of claim 17, wherein the page earcon includes speech dialog indicating the receipt of the at least one update.

19. The method of claim 1, wherein the speech input includes speech commands selected from the group of commands consisting of a selection command, a document command, a review command, a record command, a page command, or a general command.

20. The method of claim 1, wherein the selected interaction type is a document command and includes a sub-command for documenting a current weight of a resident, and wherein the speech dialog is an interrogatory regarding verification that the user is documenting the current weight of the resident.

21. The method of claim 1, further comprising:
determining, from an additional speech input of the user captured by the voice assistant device, the current weight of the resident;
comparing the determined current weight to a past weight for the resident; and
immediately providing a speech dialog regarding reweighing the resident based on the comparison of the current weight and the past weight.

22. The method of claim 21, wherein comparing the determined current weight to a past weight for the resident includes:
calculating a difference between the current weight and the past weight; and
comparing the difference to a predetermined value.

23. The method of claim 22, further comprising:
in response to determining that the difference exceeds the predetermined value, immediately providing a speech dialog with the user regarding reweighing the resident.

24. The method of claim 22, further comprising:
in response to determining that the difference does not exceed the predetermined value, providing a speech dialog with the user indicating the current weight.

25. The method of claim 21, further comprising:
determining whether an additional speech input of the user captured by the voice assistant is associated with a valid weight.

26. The method of claim 25, further comprising:
in response to determining that the additional speech input is not associated with a valid weight, providing an additional speech dialog indicating that the additional speech input is associated with an invalid weight.

27. The method of claim 25, further comprising:
in response to determining that the additional speech input is associated with a valid weight, providing an additional speech dialog indicating that the additional speech input is associated with a valid weight.

28. A method of assisting a user in providing care to residents of a care facility, the method comprising:
capturing speech input from a user with a voice assistant device carried by a user and providing speech processing, including speech recognition, at the voice assistant device;
determining, from the processed speech input of the user, a current weight associated with a resident;
associating the current weight with a care plan using the voice assistant device, the care plan being associated with the resident;
comparing the current weight to a past weight for the resident, the past weight associated with the resident and the care plan; and
immediately providing a speech dialog with the user regarding further work with the resident based on the comparison of the current weight and the past weight.

29. The method of claim 28, wherein comparing the determined current weight to a past weight for the resident includes:
calculating a difference between the current weight and the past weight; and
comparing the difference to a predetermined value.

30. The method of claim 29, further comprising:
in response to determining that the difference exceeds the predetermined value, immediately providing a speech dialog with the user regarding reweighing the resident.

31. The method of claim 29, further comprising:
in response to determining that the difference does not exceed the predetermined value, providing a speech dialog to the user indicating the current weight.

32. The method of claim 28, further comprising:
determining whether an additional speech input of the user captured by the voice assistant is associated with a valid weight.

33. The method of claim 32, further comprising:
in response to determining that the additional speech input is not associated with a valid weight, providing an additional speech dialog indicating that the additional speech input is associated with an invalid weight.

34. The method of claim 32, further comprising:
in response to determining that the additional speech input is associated with a valid weight, providing an additional speech dialog indicating that the additional speech input is associated with a valid weight.

35. The method of claim 28, wherein the speech dialog regarding the further work with the resident includes a speech dialog to direct reweighing the resident and the method further comprises receiving speech input of the user associated with the results of the reweighing step and converting the speech input of the user into machine readable input.

36. An apparatus for assisting a user in providing care to residents of a care facility, comprising:
a portable device configured to be carried by a user, the portable device configured for storing at least one care plan thereon, the care plan defining a plurality of tasks to be performed by a user as part of a workflow in providing care to the residents the portable device further configured to provide speech recognition and speech synthesis and to determine a selected interaction with a care plan from speech input of the user and to provide a speech dialog with the user in response to the selected interaction, the speech dialog being associated with the care plan, the portable device configured for processing a speech command of the speech input for selecting a type of interaction with the care plan and for processing at least one subsequent speech sub-command of the speech input reflective of tasks that are performed by the user or of care provided according to a pertinent part of the care plan, the device providing a plurality of earcons at selected times in the course of the speech dialog, the earcons having individual audible tones for indicating the existence of at least one of an active page or reminder for the user or the lack of said active page or reminder.

37. The apparatus of claim 36, wherein the care plan is associated with at least one resident of a care facility or medical facility.

38. The apparatus of claim 37, wherein the portable device is configured for documenting at least one of the care or treatment of the resident.

39. The apparatus of claim 36, wherein the speech dialog assists with identifying information to be input through speech input of the user.

40. The apparatus of claim 36, wherein the speech dialog includes an interrogatory for identifying information to be input through speech input of the user.

41. The apparatus of claim 36, further configured to process input speech to request any care plans associated with the user.

42. The apparatus of claim 36, wherein the speech input includes an interrogatory selected from the group of interrogatories consisting of: an interrogatory regarding at least one resident cared for by the user, an interrogatory regarding at least one resident that needs their vital signs documented, an interrogatory regarding at least one resident that is associated with an update, an interrogatory regarding at least one resident that needs restorative care, an interrogatory regarding at least one resident that needs care, an interrogatory regarding at least one resident that needs bathing, an interrogatory regarding the most important tasks currently assigned to the user, an interrogatory regarding recent changes to at least one of tasks or at least one resident currently assigned to the user, an interrogatory regarding tasks that are yet to be completed that are in turn associated with the user, an interrogatory regarding tasks that are scheduled that are in turn associated with the user, an interrogatory regarding the identity of another user assigned to at least one resident, or an interrogatory regarding the contents of a shift report from a previous shift.

43. The apparatus of claim 36, wherein the speech input of the user includes an interrogatory that includes at least one situational awareness question to make a user aware of the tasks of their workflow for at least one resident, the program code further configured to answer the situational awareness question with a speech dialog.

44. The apparatus of claim 36, further configured to provide a page earcon with a unique tone to indicate an outstanding page for the user in response to determining that there is an outstanding page associated with the user.

45. The apparatus of claim 44, wherein the page earcon includes a speech dialog indicating the number of outstanding pages for the user.

46. The apparatus of claim 44, further configured to determine, from an additional speech input of the user, an interaction to play the outstanding page and to play the outstanding page in response to determining the interaction to play the outstanding page.

47. The apparatus of claim 36, further configured to provide a reminder earcon with a unique tone to indicate an outstanding reminder for the user in response to determining that there is an outstanding reminder associated with the user.

48. The apparatus of claim 47, wherein the reminder earcon includes a speech dialog indicating the number of outstanding reminders for the user.

49. The apparatus of claim 47, further configured to determine, from an additional speech input of the user, an interaction to play the outstanding reminder and to play the outstanding reminder in response to determining the interaction to play the outstanding reminder.

50. The apparatus of claim 36, wherein the program code is further configured to provide an all clear earcon with a unique tone to indicate that there are no outstanding reminders or pages associated with the user in response to the determining that there are no outstanding reminders or pages associated with the user.

51. The apparatus of claim 50, wherein the all clear earcon includes a speech dialog indicating that there are no outstanding reminders or pages associated with the user.

52. The apparatus of claim 36, further configured to dynamically receive at least one update to the care plan and, in response, to provide a page earcon to the user to indicate the receipt of the at least one update.

53. The apparatus of claim 52 wherein the page earcon includes a speech dialog indicating the receipt of the at least one update.

54. The apparatus of claim 36, wherein the speech input includes speech commands selected from the group of commands consisting of a selection command, a document command, a review command, a record command, a page command, or a general command.

55. The apparatus of claim 54, wherein a document command includes a sub-command for documenting a current weight of a resident, and wherein the speech dialog is an interrogatory regarding verification that the user is documenting the current weight of the resident.

56. The apparatus of claim 36, further configured to determine, from an additional speech input of the user, the current weight of the resident, to compare the determined current weight to a past weight for the resident, and to immediately provide a speech dialog regarding reweighing the resident based on the comparison of the current weight and the past weight.

57. The apparatus of claim 56, further configured to calculate a difference between the current weight and the past weight and compare the difference to a predetermined value.

58. The apparatus of claim 57, further configured to immediately provide an additional speech dialog to the user suggesting that the user reweigh the resident in response to determining that the difference exceeds the predetermined value.

59. The apparatus of claim 57, further configured to provide an additional speech dialog to the user indicating the current weight in response to determining that the difference does not exceed the predetermined value.

60. The apparatus of claim 56, further configured to determine whether an additional speech input of the user captured by the voice assistant is associated with a valid weight.

61. The apparatus of claim 60, further configured to provide an additional speech dialog indicating that the additional speech input is associated with an invalid weight in response to determining that the additional speech input is not associated with a valid weight.

62. The apparatus of claim 60, further configured to provide an additional speech dialog indicating that the additional speech input is associated with a valid weight in response to determining that the additional speech input is associated with a valid weight.

63. An apparatus for assisting a user in providing care to residents of a care facility, comprising:
a portable device configured to be carried by a user, the portable device configured for determining, from speech input of a user, a current weight associated with a resident, associating the current weight with a care plan that is associated with the resident, comparing the current weight to a past weight for the resident, the past weight associated with the resident and the care plan, and immediately providing a speech dialog with the user regarding further work with the resident based on the comparison of the current weight and the past weight.

64. The apparatus of claim 63, further configured to calculate a difference between the current weight and the past weight and compare the difference to a predetermined value.

65. The apparatus of claim 64, further configured to immediately provide a speech dialog to the user suggesting that the user reweigh the resident in response to determining that the difference exceeds the predetermined value.

66. The apparatus of claim 64, further configured to immediately provide a speech dialog to the user indicating the current weight in response to determining that the variance does not exceed the predetermined value.

67. The apparatus of claim 63, further configured to determine whether an additional speech input of the user captured by the voice assistant is associated with a valid weight.

68. The apparatus of claim 66, further configured to provide an additional speech dialog indicating that the additional speech input is associated with an invalid weight in response to determining that the additional speech input is not associated with a valid weight.

69. The apparatus of claim 66, further configured to provide an additional speech dialog indicating that the additional speech input is associated with a valid weight in response to determining that the additional speech input is associated with a valid weight.

70. The apparatus of claim 63, further configured to immediately provide a speech dialog with the user regarding reweighinq the resident, to receive speech input of the user associated with reweighing, and to convert the speech input of the user into machine readable input.

* * * * *

UNITED STATES PATENT AND TRADEMARK OFFICE
CERTIFICATE OF CORRECTION

PATENT NO. : 8,255,225 B2  
APPLICATION NO. : 12/536696  
DATED : August 28, 2012  
INVENTOR(S) : Roger Graham Byford et al.

Page 1 of 2

It is certified that error appears in the above-identified patent and that said Letters Patent is hereby corrected as shown below:

On the Title Page item (57),
In Column 2, Abstract, last 2 lines read "... regarding reweighting the resident ..." and should read --... regarding reweighing the resident ....--.

In the Specification,
In Column 1, Line 65 reads "... equipment to Juggle or ..." and should read --equipment to juggle or ...--.

In Column 3, Line 11 reads "... input of the use, ..." and should read --input of the user ....--.

In Column 3, Lines 25-26 read "... drawings, which are incorporated in and constitute a pall of this specifications illustrate embodiments of ..." and should read --... drawings, which are which are incorporated in and constitute a part of this specification illustrate embodiments of ...--.

In Column 6, Line 22 reads "... pull-down, menus, boxes, etc." and should read --... pull-down menus, boxes, etc.--.

In Column 6, Line 50 reads "... may set tip and/or update the ..." and should read --... may set up and/or update the ...--.

In Column 7, Line 44 reads "... the power on and off Furthermore, ..." and should read --... the power on and off. Furthermore, ...--.

In Column 8, Line 44 reads "one or moose items may be ..." and should read --one or more items may be ...--.

In Column 8, Lines 61-62 read "... to convent the speech input into ..." and should read --... to convert the speech input into ...--.

Signed and Sealed this
Fifteenth Day of September, 2015

Michelle K. Lee
*Director of the United States Patent and Trademark Office*

CERTIFICATE OF CORRECTION (continued)
U.S. Pat. No. 8,255,225 B2

In Column 9, Line 49 reads ". . . may be configured communicate . . ." and should read --. . . may be configured to communicate . . .--.

In Column 10, Line 51 reads "Those skilled in the all . . ." and should read --Those skilled in the art . . .--.

In Column 13, Lines 10-11 read ". . . all audible tone may be provided . . ." and should read --. . . an audible tone may be provided . . .--.

In Column 15, Line 27 reads ". . . combinations thereof Thus, . . ." and should read --. . . combinations thereof. Thus, . . .--.

In Column 15, Line 33 reads ". . . CNA logs on ad the care plans of the . . ." and should read --. . . CNA logs on and the care plans of the . . .--.

In Column 15, Lines 37-38 reads ". . . that there a-e no active pages . . ." and should read --. . . that there are no active pages . . .--.

In Column 15, Line 51 reads ". . . during which is idle . . ." and should read --. . . during which it is idle . . .--.

In Column 18, Line 60 reads "Returning to FIG. S, each . . ." and should read --Returning to FIG 8, each . . .--.

In Column 19, Line 36 reads ". . . to sleep and /o have the . . ." and should read --. . . to sleep and/or have the . . .--.

In Column 20, Line 11 reads "Block 440 may asks the . . ." and should read --Block 440 may ask the . . .--.

In Column 21, Line 1 reads ". . . 544 and or. Similarly, if the . . ." and should read --544 and/or. Similarly, if the . . .--.

In Column 22, Line 21 reads ". . . note an or page)." and should read --. . . note and/or page).--.

In Column 22, Line 24 reads ". . . risk for fails due to the . . ." and should read --. . . risk for falls due to the . . .--.

In the Claims,
In Column 28, Line 42, CLAIM 68 reads "The apparatus of claim 66, . . ." and should read --The apparatus of claim 67.--.

In Column 28, Line 47, CLAIM 69 reads "The apparatus of claim 66, . . ." and should read --The apparatus of claim 67, . . .--.